US012714357B2

(12) United States Patent
Strasfeld et al.

(10) Patent No.: US 12,714,357 B2
(45) **Date of Patent: *Aug. 25, 2026**

(54) WOUND CARE DIAGNOSIS WITH FLUORESCENCE

(71) Applicant: Precision Healing LLC, Newton, MA (US)

(72) Inventors: David B Strasfeld, Somerville, MA (US); Ira M Herman, Boston, MA (US); W David Lee, Brookline, MA (US); Ryan Daniel Williams, Somerville, MA (US); Sean Madden, Arlington, MA (US)

(73) Assignee: Precision Healing LLC, Newton, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/794,028

(22) Filed: Aug. 5, 2024

(65) Prior Publication Data

US 2024/0389931 A1 Nov. 28, 2024

Related U.S. Application Data

(63) Continuation-in-part of application No. 17/155,141, filed on Jan. 22, 2021, now Pat. No. 12,053,262.

(Continued)

(51) Int. Cl.
*A61B 5/00* (2006.01)

(52) U.S. Cl.
CPC ............ *A61B 5/445* (2013.01); *A61B 5/0071* (2013.01); *A61B 5/0075* (2013.01); *A61B 5/443* (2013.01)

(58) Field of Classification Search
CPC ..... A61B 5/445; A61B 5/0071; A61B 5/0075; A61B 5/443
See application file for complete search history.

(56) References Cited

U.S. PATENT DOCUMENTS 5,553,616 A * 9/1996 Ham ...................... G01N 21/65 250/341.1
5,701,902 A * 12/1997 Vari ..................... A61B 5/0059 600/476

(Continued)

OTHER PUBLICATIONS

Niu, L., Zhao, F., Chen, J., Nong, J., Wang, C., Wang, J., . . . & Hu, S. (2018). Isothermal amplification and rapid detection of Klebsiella pneumoniae based on the multiple cross displacement amplification (MCDA) and gold nanoparticle lateral flow biosensor (LFB). Plos one, 13(10), e0204332.

*Primary Examiner* — Sanjay Cattungal
(74) *Attorney, Agent, or Firm* — Adams Intellex, PLC

(57) ABSTRACT

A plurality of optical excitation ultraviolet light wavelength bands is scanned on a wound sample. The material sample exhibits optical spectral characteristics along the light wavelength spectrum. Excitation response wavelengths emitted by the wound sample are captured in response to the plurality of optical excitation ultraviolet light wavelength bands. The capturing is accomplished using an image sensor. Output values of a plurality of pixels of an image from the image sensor are measured. The image represents excitation response wavelengths captured by the image sensor. The measuring detects optical spectral characteristics of the wound sample, and the optical spectral characteristics are in response to the plurality of optical excitation light wavelength bands. An output signature indicative of composition of a condition of the wound sample is provided, wherein the condition of the wound sample provides a metric of wound monitoring.

25 Claims, 10 Drawing Sheets

Related U.S. Application Data

(60) Provisional application No. 63/550,096, filed on Feb. 6, 2024, provisional application No. 63/132,541, filed on Dec. 31, 2020, provisional application No. 62/964,969, filed on Jan. 23, 2020.

(56) References Cited

U.S. PATENT DOCUMENTS 5,784,162 A * 7/1998 Cabib ..................... G01J 3/453 435/6.12
6,205,354 B1 * 3/2001 Gellermann ......... A61B 5/1455 356/301
6,998,247 B2 * 2/2006 Monfre ................ G01N 21/359 435/14
8,025,851 B2 9/2011 Slowey et al.
8,385,615 B2 * 2/2013 Levenson .......... G01N 21/6486 600/407
8,634,607 B2 * 1/2014 Levenson .......... G01N 21/6456 600/475
10,146,912 B2 12/2018 Drysdale et al.
10,299,965 B1 5/2019 Brar
10,376,148 B2 8/2019 Wood et al.
10,438,356 B2 10/2019 Dacosta
10,517,483 B2 12/2019 Wood et al.
10,618,983 B2 4/2020 Mitragotri et al.
10,783,632 B2 9/2020 Fan et al.
2002/0016534 A1 * 2/2002 Trepagnier ........... A61B 5/0062 600/316
2002/0082487 A1 * 6/2002 Kollias ................ A61B 5/1455 600/316
2002/0091324 A1 * 7/2002 Kollias ................ A61B 5/0071 600/476
2005/0131304 A1 * 6/2005 Stamatas ................ G01N 21/64 600/476
2006/0092315 A1 * 5/2006 Payonk .................. A61B 5/445 348/370
2007/0173725 A1 7/2007 Souta et al.
2007/0265532 A1 * 11/2007 Maynard ............ A61B 5/14532 600/477
2007/0276199 A1 * 11/2007 Ediger ................. A61B 5/0071 600/300
2008/0076985 A1 * 3/2008 Matousek ............ A61B 5/0075 600/310
2008/0214460 A1 9/2008 Neuberger et al.
2009/0137908 A1 * 5/2009 Patwardhan ........... A61B 5/444 600/476
2009/0162423 A1 6/2009 Neuberger et al.
2010/0168586 A1 * 7/2010 Hillman ............... A61B 5/0064 348/E13.001
2011/0021973 A1 1/2011 Neuberger et al.
2011/0039342 A1 2/2011 Percival et al.
2011/0117025 A1 * 5/2011 Dacosta ............. G01N 21/6486 435/5
2012/0268573 A1 * 10/2012 Schonborn ........... A61B 5/0062 348/E13.074
2013/0053677 A1 2/2013 Schoenfeld
2014/0163389 A1 6/2014 Kudenov et al.
2015/0287191 A1 * 10/2015 Koruga .................. A61B 5/444 382/128
2016/0030132 A1 2/2016 Cheung et al.
2016/0157725 A1 * 6/2016 Munoz ................... H04N 23/51 600/407
2016/0166194 A1 6/2016 Gareau et al.
2017/0160189 A1 6/2017 Priore
2017/0209493 A1 * 7/2017 Luttun ................. C12N 5/0607
2017/0236281 A1 * 8/2017 Dacosta ................ G06T 7/0016 382/128
2018/0202927 A1 7/2018 Isikman et al.
2019/0133502 A1 5/2019 Gomi et al.
2021/0268068 A1 * 9/2021 Aractingi ............. C12N 15/115

* cited by examiner

WOUND CARE DIAGNOSIS WITH FLUORESCENCE

RELATED APPLICATIONS

This application claims the benefit of U.S. provisional patent application "Wound Care Image Analysis Using A Smartphone" Ser. No. 63/550,096, filed Feb. 6, 2024.

This application is also a continuation-in-part of U.S. patent application "Skin Diagnostics Using Optical Signatures" Ser. No. 17/155,141, filed Jan. 22, 2021, which claims the benefit of U.S. provisional patent applications "Systems and Methods for Wound Care Diagnostics and Treatment" Ser. No. 62/964,969, filed Jan. 23, 2020, and "Multispectral Sample Analysis Using Fluorescence Signatures" Ser. No. 63/132,541, filed Dec. 31, 2020.

Each of the foregoing applications is hereby incorporated by reference in its entirety.

FIELD OF ART

This application relates generally to wound care diagnosis and more particularly to wound care diagnosis with fluorescence signatures.

BACKGROUND

Materials, whether natural and manufactured, are ubiquitous and support the lives of people worldwide. A material is a substance or a mixture of substances that make up a given object. Materials are used in the manufacture of clothing, shelter, vehicles, and many other items. Clothing comprising various materials is worn to cover or protect, and to keep cool or warm. The clothing also makes statements about class, culture, origin, and beliefs. Structures are constructed to provide shelter, and are based on purpose, design, and available materials. Materials used in vehicles enable transportation. A given object can be formed from materials based on one or more substances. Common materials include wood, plastic, metal, fabric, and glass. Material properties that are of particular interest include physical properties such as state, where material state includes solid, liquid, gas, or plasma states. Other physical properties include the density of the material and magnetic characteristics of the material. The material properties of interest further include chemical properties such as chemical resistance of the material to attack by other chemicals, and the combustibility of the material. The material properties can further include mechanical properties such as malleability, ductility, and strength; and electrical properties such as conductivity and resistivity. The properties of a material can also include optical properties such as transmissivity and absorptivity. Still other properties can be used. Because each material has its own unique set of properties, the physical, chemical, mechanical, electrical, optical, and other responses of a material can be analyzed to characterize and identify unknown materials.

Analysis and characterization tasks are performed on materials associated with industries including manufacturing, aerospace, and taxonomy, to name only a few. These same tasks are also utilized in research applications. The tasks identify a material or materials within a sample, characterize new alloys or compounds of materials, and so on. The analysis and characterization tasks are further used to identify the presence of unexpected materials within a sample. The unexpected materials within a sample can include contaminants or impurities. The presence of contaminants within materials is generally considered undesirable as contaminants can cause systems made from the materials to fail. Another class of materials analysis uses sophisticated testing procedures and advanced testing techniques to obtain detailed information about a material or sample. The detailed information can include identification of the chemical composition of the material. This latter class of materials analysis requires complex laboratory equipment and advanced training. Determination of material surface topology and composition can be accomplished using a scanning electron microscope (SEM), which uses a beam of electrons, while a transmission electron microscope (TEM) can be used in crystalline defect analysis to predict material behavior and to find failure mechanisms. Also, X-ray Diffraction (XRD) is used to identify and characterize crystalline materials. These complicated and expensive tests, techniques, and types of equipment, which are usually available only in laboratories, can be used alone or in combination to characterize and identify unknown materials.

SUMMARY

Disclosed techniques can perform wound care diagnosis using one or more optical excitation light wavelength bands. Techniques for wound diagnostics using optical output signatures disclosed herein use light from a range of wavelengths across the electromagnetic spectrum. The range of wavelengths corresponds to various types of light such as infrared (IR) light, long-wavelength IR (LWIR) light, visible light, and so on. The wavelengths can also include those that correspond to thermal energy. A plurality of optical excitation ultraviolet light wavelength bands excites electrons in molecules of a wound sample and cause the electrons to emit light or fluoresce. Excitation response wavelengths emitted by the scanned wound sample are captured with an image sensor. The image sensor can include a broad-spectrum image sensor and low-cost optical filtering techniques, such as a color gel or dielectric filter. The broad-spectrum image sensor provides sensitivities to particular wavelengths, including light frequencies which are visible to the human eye, and light frequencies which are not (e.g., IR, thermal). Wound samples contain elements that reflect and absorb light differently at different wavelengths, resulting in different fluorescence signatures. Thus, wound care diagnosis with fluorescence signatures can be used to differentiate wound healing states based on their excitation output signatures, including their fluorescence characteristics, their light reflection characteristics, their light absorption characteristics, and even their light transmission characteristics.

Disclosed techniques address a method for wound care diagnosis using fluorescence signatures. The disclosed techniques enable development of wound monitoring and wound care strategies based on output signatures generated from captured wound sample excitation response wavelengths. A plurality of optical excitation ultraviolet light wavelength bands on a wound sample is scanned. The wound sample that is scanned exhibits optical spectral characteristics along the light wavelength spectrum. The optical excitation light wavelength bands and the exhibited optical spectral characteristics of the material sample can include ultraviolet (UV) light, visible light such as Red-Green-Blue (RGB) light, IR light, long-wavelength IR light, fluorescent light, and so on. The wound sample can include cells, tissues, and organs. The wound sample can include wound exudate, debrided tissue, etc. Excitation response wavelengths emitted by the wound sample are captured in response to the plurality of optical excitation ultraviolet light wavelength bands. The capturing is accomplished using an image sensor such as UV sensor. The image sensor can also include an IR sensor, a thermal sensor, an RGB sensor, and the like. Output values of a plurality of pixels of an image from the image sensor are measured. The output values can be represented by analog or digital signals. The image from which pixel values are measured represents excitation response wavelengths captured by the image sensor. The measuring detects optical spectral characteristics of the wound sample, and the optical spectral characteristics are in response to the plurality of optical excitation light wavelength bands. The plurality of optical excitation light wavelength bands can include one or more non-fluorescent optical excitation light wavelength bands, where more non-fluorescent optical excitation light wavelength bands coincide with one or more absorption wavelength maximums of wound sample constituents.

An output signature that is indicative of a condition of the wound sample is generated. The output signature is based on interpreting the output values that were measured. The output signature can be indicative of the presence of nicotinamide adenine dinucleotide plus hydrogen (NADH) and flavins, the presence of collagen, the presence of porphyrins, the presence of infection, etc. The condition of the wound sample provides a metric of wound monitoring. The output signature can be regenerated over time. The regenerating the output signature over time informs a wound care treatment plan.

A method for wound care diagnosis is disclosed comprising: scanning a plurality of optical excitation ultraviolet light wavelength bands on a wound sample, wherein the wound sample exhibits optical spectral characteristics along the light wavelength spectrum; capturing excitation response wavelengths emitted by the wound sample in response to the plurality of optical excitation ultraviolet light wavelength bands, wherein the capturing is accomplished using an image sensor; measuring output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generating an output signature indicative of a condition of the wound sample, wherein the condition of the wound sample provides a metric of wound monitoring.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
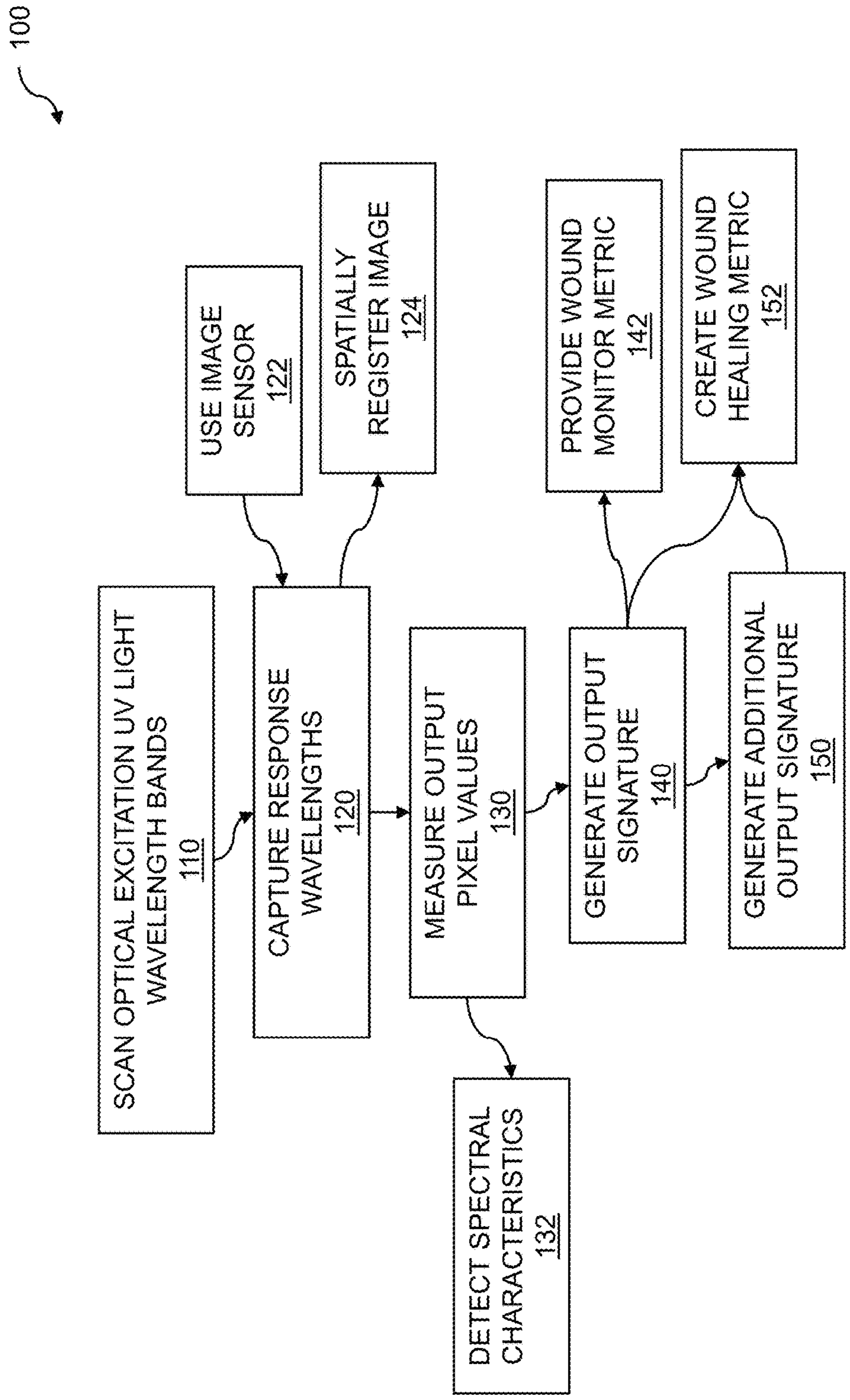
FIG. 1 is a flow diagram for wound care diagnosis with fluorescence signatures.

Techniques for wound care diagnosis with fluorescence signatures are disclosed. The techniques include capturing excitation response wavelengths emitted by a wound sample. The excitation response wavelengths can be captured using an image sensor. The image sensor can include a commercial off the shelf (COTS) sensor such as an ultraviolet (UV) sensor, a red-green-blue (RGB) sensor, an infrared (IR) sensor, etc. Output values of pixels associated with an image captured are measured by the image sensor. The image from the image sensor represents excitation response wavelengths from the wound sample. The excitation response wavelengths result from scanning the wound sample with a plurality of optical excitation ultraviolet light wavelength bands. An output signature that is indicative of a condition of the wound sample is generated. The output signature is based on light wavelength fluorescence of a material sample resulting from exciting the wound sample with at least one light wavelength. The at least one light wavelength can be provided by an external light source. The external light source can emit at least one wavelength of light. The light can be based on light along the UV light wavelength spectrum. The light can further be based on what is commonly called visible light or RGB light, to longer wavelengths that include what is commonly called infrared light. This technique uses light from a range of wavelengths across the electromagnetic spectrum to determine light fluorescence by a wound sample.

The fluorescence characteristics of the wound sample are determined in response to a plurality of ultraviolet excitation light wavelength bands. The light excitation causes molecules of a compound within the wound sample to fluoresce light wavelengths. The light fluoresced by the wound can be detected by a sensor such as a UV sensor. One or more UV sensors can be used to capture the fluorescent excitation response wavelengths. The sensors can further include one or more of RGB sensors, IR sensors, and the like. The sensors can include integrated sensors. The sensors, which when taken together can include a broad-spectrum sensor, can employ an integrated, very low-cost Bayer filter which enables the broad-spectrum image sensor to provide sensitivities to particular wavelengths, including light from frequencies which are visible to the human eye and those which are not. Various materials fluoresce and reflect different wavelengths of light when compared to one another. However, imaging such as multispectral imaging can be used to differentiate contents of a wound based on their spectral fluorescence signatures and characteristics. Such differentiation enables wound care diagnosis. As disclosed, wound care diagnosis based on output signatures can reduce the complexity, cost, and deployment challenges when compared to using specialized multispectral cameras, elaborate optical filters, and expensive filter wheels. The filter wheels can have significant orientation and alignment sensitivities.

The method of wound care diagnosis with fluorescence disclosed herein uses ultraviolet wavelength bands to scan a wound sample. The scanning light causes the wound sample to exhibit optical spectral characteristics such as absorption, emission, and fluorescence along the light wavelength spectrum. This excitation response of the wound sample to the scanned ultraviolet light is captured as pixels using an image sensor. The image sensor can include an integrated sensor, where the integrated sensor can include one or more ultraviolet sensors, one or more of a Red-Green-Blue (RGB) sensor and an infrared (IR) sensor, and so on. The sensor can include an ordinary, readily available sensor. The sensor can include one or more sensors selected for specific frequencies such as 365 nm and 395 nm. The pixel values of the captured excitation response or image are measured, where the measuring detects optical spectral characteristics of the wound sample.

The sensors used typically include mass produced sensors that have applications in low-cost technology that endeavors to detect light waves in the IR spectrum, suitable for digital processing. The sensor can employ an integrated Bayer filter applied during the manufacturing process of a CMOS, CCD, or similar sensor semiconductor fabrication. The Bayer filter is completely integrated within or to the sensor and cannot be removed, replaced, or adjusted. When light impinges the surface of a sensor, the underlying photosensors register a signal related to the intensity of the impinging wavelengths as a function of the color of the integrated filter directly over each photosensor device. The disclosed technology does not require expensive special cameras; filter wheels; complex optical alignments; or stationary, non-handheld components.

FIG. 1 is a flow diagram for wound care diagnosis with fluorescence signatures. Wound care diagnosis of a wound such as a skin wound can be enabled by image analysis. A plurality of optical excitation ultraviolet light wavelength bands is scanned on a wound sample. The wound sample exhibits optical spectral characteristics along the light wavelength spectrum. Excitation response wavelengths are captured. The excitation response wavelengths are emitted by the wound sample in response to the plurality of optical excitation ultraviolet light wavelength bands. The capturing is accomplished using an image sensor. Output values of a plurality of pixels of an image from the image sensor are measured. The image represents the excitation response wavelengths captured by the image sensor. The measuring detects optical spectral characteristics of the wound sample. The optical spectral characteristics are in response to the plurality of optical excitation light wavelength bands. An output signature is generated that is indicative of a condition of the wound sample. The condition of the wound sample provides a metric of wound monitoring.

The flow 100 includes scanning a plurality of optical ultraviolet excitation light wavelength bands 110 on a wound sample. The wound sample can include cells, tissues, and organs. The wound sample can include healthy cells, tissues, and organs or damaged cells, tissues, and organs. The wound sample can include tissue from a wound, wound exudate, etc. The wound sample that is scanned exhibits optical spectral characteristics along the light wavelength spectrum. The optical spectral characteristics can include absorption and/or emission. The optical spectral characteristics that are exhibited can include fluorescence characteristics. The fluorescence characteristics can occur at the same wavelength as the excitation light, or at a different wavelength. The scanned material can exhibit other optical qualities. The plurality of optical excitation light wavelength bands can include one or more non-fluorescent optical excitation light wavelength bands. Based on the type of material associated with a wound that is scanned, one or more non-fluorescent optical excitation light wavelength bands can coincide with one or more absorption wavelength maximums of wound constituents (discussed below).

The optical excitation light wavelength bands can include the ultraviolet (UV) bands, infrared (IR) bands, visible light bands (e.g., red-green-blue, or RGB), long-wavelength IR (LWIR) bands, thermal bands, and so on. In embodiments, the excitation response wavelengths comprise wavelengths substantially in a range of 440 nm to 500 nm and 500 nm to 550 nm. The excitation response wavelengths are in response to the optical excitation ultraviolet light wavelength bands. A band of the plurality of optical excitation light wavelength bands can include wavelengths substantially in the range of 325 nm to 375 nm, a second band of the plurality of optical excitation light wavelength bands can include wavelengths substantially in the range of 350 nm to 400 nm, a third band of the plurality of optical excitation light wavelength bands can include wavelengths substantially in the range of 375 nm to 425 nm, etc. Other bands can also be used. A fourth band of optical excitation light wavelength bands comprises wavelengths substantially in the range of 400 nm to 450 nm. The optical excitation light wavelength bands can include wide bands or narrow bands. In a usage example, the excitation wavelengths can include 365 nm and 395 nm. The plurality of optical excitation light wavelength bands can include narrow bands substantially at 350 nm, 375 nm, 400 nm, 425 nm, 450 nm, 500 nm, 525 nm, 550 nm, 575 nm, 600 nm, 625 nm, and so on.

The flow 100 includes capturing excitation response wavelengths 120 emitted by the wound sample in response to the plurality of optical excitation ultraviolet light wavelength bands. The excitation response wavelengths can include one or more wavelengths. In embodiments, the excitation response wavelengths can include a fluorescence signature for the wound sample. The fluorescence signature can be used to determine one or more wound characteristics associated with the wound sample. In the flow 100, the capturing is accomplished using an image sensor 122. The image sensor can include a UV sensor, an IR sensor, a thermal sensor, and so on. The sensor can include an RGB sensor. The sensor can produce analog or digital output signals. The output values of a sensor, such as an RGB sensor, can include electrical signals, and thus the RGB sensor translates wavelength intensity to an electrical representation by providing three output values: a red output value, a green output value, and a blue output value. Similarly, UV sensors and IR sensors can produce electrical signals that represent wavelength intensity by converting the intensities to electrical sensors. These sensors generally demonstrate peak blue sensitivity at 400-475 nm, peak green sensitivity at 475-580 nm, and peak red sensitivity at 580-750 nm. In order to avoid signal contribution from an excitation LED (or other excitation source) that has a long red tail that may be detected by the spectral channels built into the RGB imager, the excitation source may be outfitted with a bandpass filter that prevents crosstalk. Additionally, a long-pass filter placed in front of the RGB sensor further prevents a spurious signal from the excitation LED. The flow 100 further includes spatially registering the image 124 to determine wound features contained in the wound sample. Various wound features can be determined. In embodiments, the wound features can include a wound center and a wound edge. The wound features can further include a wound depth. In a usage example, the spatially registering the image can include locating a wound, locating a wound edge, locating a wound center, etc. The capturing can further include comparing image resolution at a plurality of narrow optical excitation light wavelength bands. The comparing image resolution at narrow wavelength bands can provide further information associated with the wound sample. The comparing can enable wound depth analysis.

The flow 100 includes measuring output values 130 of a plurality of pixels of an image from the image sensor. The measuring output values can be based on measuring emission, fluorescence, absorption (e.g., attenuation), and so on. The image from which pixels are measured can represent excitation response wavelengths captured by the image sensor. Further, the measuring output values can include measurements at the absorption wavelength maximums. In the flow 100, the measuring detects optical spectral characteristics 132 of the wound sample that was scanned. The optical spectral characteristics are measured in response to the plurality of optical excitation light wavelength bands. The measurements can occur at fluorescent wavelengths, absorption wavelengths, and so on. The measurements at the absorption wavelength maximums augment interpreting of wound status (discussed below).

The flow 100 includes generating an output signature 140 indicative of a condition of the wound sample. The output signature can include a variety of indicators and markers. The signature can be based on numerical values, a range of values, ratios, percentages, qualitative evaluations, and so on. The output signature of the wound can include microbe indications, inflammation markers, granulation markers, epithelialization markers, and remodeling markers. In the flow 100, the condition of the wound sample provides a metric 142 of wound monitoring. The output signature can enable wound care management, where wound care management can include various treatments associated with the wound. The output signature can provide a wound state or a wound healing trajectory. The wound state can include a stalled state, a healing state, a non-healing state, an infected state, an inflamed state, a granulating state, or an epithelializing state. In embodiments, the metric of wound monitoring can distinguish among wound repair, wound regeneration, and wound degeneration. The distinguishing accomplished by the monitoring can include comparing one or more ratios. In embodiments, the distinguishing can be enabled by comparing ratios of $NAD^+$ to NADH. In other embodiments, the distinguishing is enabled by comparing ratios of FAD to $FADH_2$. The output signature can be indicative of the presence or absence of various constituents within the wound sample. In embodiments, the metric of wound monitoring can enable development of a wound care strategy. The wound care strategy can include bandaging, applications, medications, etc.

The output signature can be indicative of the presence of nicotinamide adenine dinucleotide plus hydrogen (NADH) and flavins. The output signature can be indicative of the presence of collagen. The NADH, flavins, and collagen can be critical to wound healing. The output signature can be based on interpreting the output values that were measured. The interpreting can be based on output values from the image sensor, and the output values can be indicative of one or more wavelengths. The interpreting can be based on measured wavelengths substantially in the range of 325 nm to 400 nm, and 400 nm to 475 nm. Other light wavelengths can also be used. In a usage example, wavelengths of particular interest can include 365 nm and 395 nm.

The flow 100 further includes generating an additional output signature 150 indicative of a condition of the wound sample. The additional output signature can be generated based on capturing additional excitation response wavelengths emitted by an additional wound sample. The output signature and the additional output signatures can be generated contemporaneously to verify signature accuracy, at different times, and so on. In embodiments, the additional output signature can be generated at a later point in time than the output signature. The later point in time can include a number of elapsed hours, days, weeks, months, and the like. The output signature and the additional output signature can be compared. In the flow 100, the output signature and the additional output signature can be used to create a wound healing trajectory metric 152. The wound healing trajectory metric can indicate a positive trajectory (e.g., healing), a negative trajectory (e.g., not healing), a rate of healing, etc. The wound healing trajectory metric can be used for a variety of wound treatment choices and techniques. In embodiments, the wound healing trajectory metric can be used to provide a recommended treatment option. A recommended treatment option can include one or more of a bandage type, a frequency of bandage changes, use of a wound pump, a course of antibiotics, etc. In embodiments, the recommended treatment option can include a debridement recommendation. Wound debridement can include removal of necrotic tissue associated with the wound to improve wound healing.

In embodiments, the metric of wound healing can include an epithelialization metric. The epithelialization metric can describe a state or a rate of epithelialization (e.g., covering or healing) of a wound. The epithelialization metric can be used to describe wound healing progress. The epithelialization metric can be based on detecting biochemicals, detecting biochemical ratios, and so on. In embodiments, the epithelialization metric can be based on detecting nicotinamide adenine dinucleotide plus hydrogen (NADH) around the wound. The NADH transfer energy to the wound can aid healing of the wound. In embodiments, the epithelialization metric can be further based on detecting a ratio of nicotinamide adenine dinucleotide ($NAD^+$) to nicotinamide adenine dinucleotide plus hydrogen (NADH) around the wound. The $NAD^+$ to NADH ratio can indicate an amount of regulation of an intracellular redox state. In embodiments, the $NAD^+$ and/or NADH optical excitation ultraviolet light wavelength bands can include wavelengths substantially in the range of 325 nm to 400 nm.

The epithelialization metric can be based on further detection. In embodiments, the epithelialization metric can be further based on detecting oxidized flavin adenine dinucleotide (FAD) around the wound. Among other functions, FAD can maintain the redox states of cells. In embodiments, the epithelialization metric can be further based on detecting a ratio of flavin adenine dinucleotide (FAD) to its reduced form ($FADH_2$) around the wound. In embodiments, the FAD and/or $FADH_2$ optical excitation ultraviolet light wavelength bands can include additional wavelengths substantially in the range of 400 nm to 475 nm. In further embodiments, the epithelialization metric can define a spatial halo around a healing perimeter of the wound. The spatial halo around the healing perimeter can be based on a wavelength of light. In embodiments, the spatial halo can include a blue light wavelength ring. The blue light wavelength ring can be captured using an image sensor.

Various steps in the flow 100 may be changed in order, repeated, omitted, or the like without departing from the disclosed concepts. Various embodiments of the flow 100 can be included in a computer program product embodied in a non-transitory computer readable medium that includes code executable by one or more processors.

Figure 2:
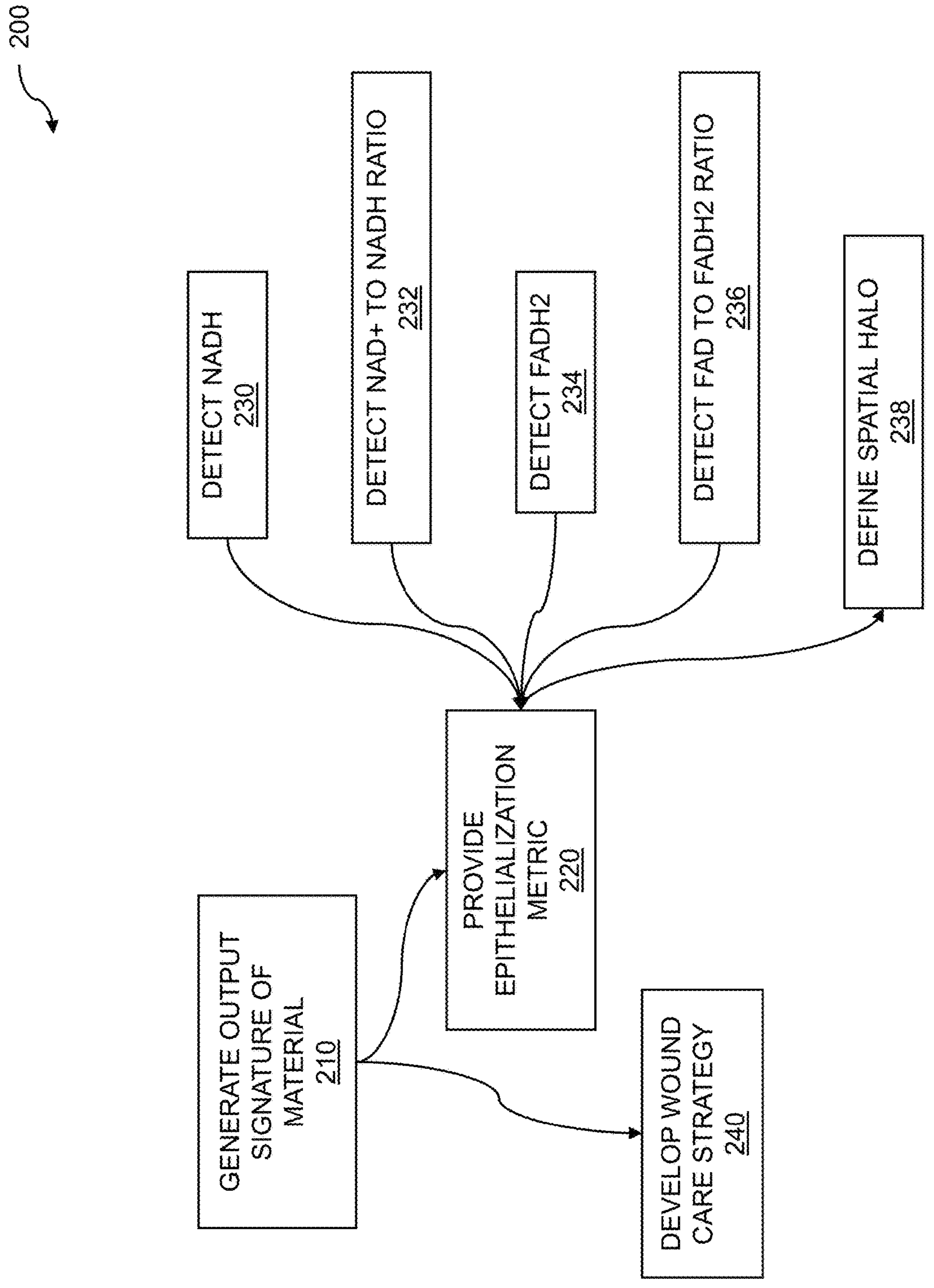
FIG. 2 is a flow diagram for providing an epithelialization metric.

FIG. 2 is a flow diagram for providing an epithelialization metric. The providing an epithelialization metric can be accomplished in response to illumination of a material sample such as a wound sample. The illumination of the sample can be accomplished using optical excitation ultraviolet light wavelength bands emitted by a light source.

Output values of a plurality of pixels of an image can be captured using an image sensor. The external light source can illuminate a material sample, where the material sample can include living tissue, tissue associated with a wound, wound exudate, and so on. The generated epithelialization metric enables wound care diagnosis with fluorescence signatures. A plurality of optical excitation ultraviolet light wavelength bands on a wound sample is scanned. The wound sample exhibits optical spectral characteristics along the light wavelength spectrum. Excitation response wavelengths are captured. The excitation response wavelengths are emitted by the wound sample in response to the plurality of optical excitation ultraviolet light wavelength bands. The capturing is accomplished using an image sensor. Output values of a plurality of pixels of an image from the image sensor are measured. The image represents the excitation response wavelengths captured by the image sensor. The measuring detects optical spectral characteristics of the wound sample, and the optical spectral characteristics are in response to the plurality of optical excitation light wavelength bands. An output signature that is indicative of a condition of the wound sample is generated. The condition of the wound sample provides a metric of wound monitoring.

Wound healing is a principal concern of healthcare professionals providing wound treatment to patients. A wound, which can include a break in skin or other body tissues associated with the patient, can result from surgery, injuries, trauma injuries, disease, and so on. The healing of a wound depends on a variety of factors. The healing factors can include desiccation, infection, or unusual bacteria presence in a wound; the age of the patient as older patients tend to heal more slowly; patient body type such as thin, average, overweight, or obese since obese patients can experience poor blood circulation in adipose tissue; patient nutrition since poor nutrition can hinder healing; and other medical conditions or treatments such as an immunosuppressed patient, a patient undergoing chemotherapy or immunotherapy treatments, etc. Further, wound healing can be better characterized and enhanced by understanding what is "going on" within the wound. A visual inspection of a wound can yield some information about the state of the wound, healing progress, and so on. A visual inspection of the wound can observe edema and erythema; an examination of bandages removed from covering a wound can observe discharge associated with bleeding or suppuration; etc. However, visual examination of the wound only enables determination of a broad status of the wound rather than a detailed review of what healing-related factors are present, or what processes are occurring within the wound. A visual examination generally does not accurately or precisely quantify the status of the wound. For example, fluorescence characteristics cannot be assessed with a visual inspection. In order to determine what is going on within a wound, a generated material sample status can be based on a five-factor biophysical status. The five-factor biophysical status can include identifying wound topology, inflammation, epithelialization, granulation, and infection. These five factors can be identified based on analysis of fluorescence characteristics and reflectance characteristics of the material sample. The material sample can include material from the skin wound, exudate from the skin wound, etc.

Another technique that can be used to determine a biochemical status of a wound such as a skin wound is based on a lateral flow assay (LFA). A lateral flow assay is used to detect the presence or absence of a target analyte. The target analyte can include a pathogen, a biomarker, and so on within a sample. The LFA can be used to detect target analytes in samples obtained from humans and animals. The LFA can also be used to detect contaminants within water supplies and foodstuffs consumed by humans and animals. The LFA techniques are further used to detect diseases such as COVID-19 and are commonly used for in-home tests such as covid tests and pregnancy tests. The LFA techniques discussed herein can be based on immunoassay techniques. An immunoassay technique can use a membrane such as a nitrocellulose membrane to which a sample can be supplied. The sample can include a liquid, where the liquid can include a complex liquid. In addition to the nitrocellulose membrane, the LFA can include nanoparticles or other particles or molecules that have been dyed or colored, and antibodies that target specific analytes and can be characterized visually or optically to provide qualitative, semi-quantitative, or quantitative results. The LFAs may include one or more antibodies that target one or more regions of the analyte in a sandwich or competitive scheme. The LFA may also include a sample pad which includes chemical additives to increase the performance of the immunoassay. The LFA typically includes a "control" that can be used to indicate that the test is working as expected. The control can be indicated by a color bar on the nitrocellulose membrane. The presence of analytes within the test sample can also be indicated by a color bar on the nitrocellulose membrane. The biophysical result is based on analysis of the fluorescence characteristics and the reflectance characteristics associated with the material sample.

Identification of water content within a wound such as a skin wound further assists in determining the biophysical status of the skin wound. The water content can be linked to a signature such as an inflammation signature associated with a wound. The inflammation signature can be associated with the status of wound healing. Unlike most biochromes, water exhibits a monotonically increasing absorption characteristic across an excitation profile as the excitation wavelength increases. Because water is such an integral component of living tissue, water identification can be very useful. Determining the water content within a wound can be accomplished by monitoring light wavelength absorption at 800 nm to 1000 nm and comparing the light wavelength absorption to absorption at shorter wavelengths. The absorption can be determined based on a reduction in reflectance as detected by a sensor such as a Red-Green-Blue (RGB) sensor. Absorption by most chromophores found in nature decreases with increasing wavelengths; however, in the case of water, the opposite is true. A light source with peak intensity from 800 nm to 1000 nm can be used to generate an absorption signal based on a comparison to a diffuse reflectance standard:

$$\text{Absorption Image} = -\log\left(\frac{(\text{Raw Image}-\text{Dark Image})/\text{Exp}}{(DR\ \text{Image}-\text{Dark Image})/\text{Exp}}\right)$$

where Exp is the exposure time, the Raw Image is the output of the RGB sensor with excitation light illumination as described herein, the Dark Image is the output of the RGB sensor with no excitation light illumination and only ambient lighting conditions, and the DR (diffuse reflectance) Image standard is a known and characterized sample that provides a baseline output of the RGB sensor with excitation light illumination.

The flow 200 can include generating 210 an output signature indicative of a condition of the wound sample. The output signature can be generated from the measured output values of pixels of an image from the image sensor. Recall that the image sensor can include an RGB sensor, a UV sensor, and so on. The image sensor can include one or more filters that enable the sensor to measure the collected light such as UV light. The generated output signature can be based on a set of measured sensor output values, a plurality of sets of generated output signatures, etc. Further embodiments can include generating an additional output signature indicative of a condition of the wound sample. The second generated output signature can be compared to the generated signature that was based on initially measured output values. In embodiments, the additional output signature can be generated at a later point in time than the output signature.

Discussed previously and throughout, an output signature that is indicative of a condition of the wound sample can be generated. The output signature is generated based on the measured output values of pixels associated with an image. The image is provided by an image sensor which is used to capture excitation response wavelengths emitted by the wound sample in response to optical excitation ultraviolet light wavelength bands. In embodiments, the condition of the wound sample can provide a metric of wound monitoring. The wound monitoring can be used to distinguish among healing states associated with the wound. In embodiments, the metric of wound monitoring distinguishes among wound repair, wound regeneration, and wound degeneration. In the flow 200, the metric of wound healing comprises an epithelialization metric 220. The epithelial tissue is one of four types of body tissue. Epithelial tissue covers internal organs, interior surfaces, and external surfaces of the body. Epithelial cells are present in a wound to aid the wound healing process. The epithelial metric can be based on one or more factors, ratios, and so on. In the flow 200, the epithelialization metric can be based on detecting 230 nicotinamide adenine dinucleotide plus hydrogen (NADH) around the wound. NADH produces energy in a body and can aid the healing processes. The flow 200 can be further based on detecting a ratio 232 of nicotinamide adenine dinucleotide ($NAD^+$) to nicotinamide adenine dinucleotide plus hydrogen (NADH) around the wound. $NAD^+$ and NADH are key factors in metabolic processes in the body that convert nutrients to energy. For example, absorption can be compared at ~340 nm and 260 nm. NADH absorbs at both of these wavelengths, while $NAD^+$ only absorbs at 260 nm. The 260 nm/340 nm absorption ratio would be much higher for $NAD^+$. When a value of the ratio of $NAD^+$ to NADH ($NAD^+$/NADH) is high, the ratio can indicate a cellular condition which is favorable to oxidation reactions. The ratio can indicate how a body is reacting to a wound and concentrating energy on healing the wound.

In the flow 200, the epithelialization metric can be further based on detecting 234 flavin adenine dinucleotide ($FADH_2$) around the wound. $FADH_2$ is a coenzyme, as is NADH, and is critical to the creation of cellular energy. The flow 200 further includes detecting a ratio 236 of flavin adenine dinucleotide (FAD) to flavin adenine dinucleotide plus hydrogen ($FADH_2$) around the wound. The ratio of FAD to $FADH_2$ (FAD/$FADH_2$) is also indicative of wound healing. For example, FAD has absorption peaks with similar intensities at 450 nm and 370 nm, while $FADH_2$ has a single absorption peak at 360 nm. Thus, if the ratio of 450 nm/370 nm is near 1.0, and there is fluorescence at 540 nm with a 400 nm excitation, that would suggest a high FAD concentration. In the flow 200, the epithelialization metric can define a spatial halo 238 around a healing perimeter of the wound. The spatial halo can include a halo of light, where the light can include excitation response wavelengths emitted by the wound sample in response to the optical excitation ultraviolet light wavelength bands. The spatial halo can be described by a geometric shape such as a circle, an oval, a square, a rectangle, etc. The spatial halo can include one or more wavelengths, colors, etc., of light. In embodiments, the spatial halo can include a blue light wavelength ring. The blue light wavelength ring can be captured using the image sensor.

Discussed previously and throughout, a wound healing metric (discussed above) can be used to generate an output signature indicative of a condition of the wound sample. In addition, the condition of the wound sample can provide a metric of wound monitoring. In the flow 200, the metric of wound monitoring can enable development 240 of a wound care strategy. The wound care strategy can include types of wound dressing such as bandages, and a frequency of checking and replacing wound dressings. The wound care strategy can include a course of antibiotics, use of a wound pump to remove excess fluid, application of heat and/or moisture to speed healing, and so on. In embodiments, the metric of wound monitoring can distinguish among wound repair, wound regeneration, and wound degeneration. Distinguishing among the various wound states can be used to adjust the wound care plan. In embodiments, the distinguishing can be enabled by comparing ratios of nicotinamide adenine dinucleotide ($NAD^+$) to nicotinamide adenine dinucleotide plus hydrogen (NADH). In further embodiments, the distinguishing can be enabled by comparing ratios of flavin adenine dinucleotide (FAD) to flavin adenine dinucleotide plus hydrogen ($FADH_2$).

The adjustment to the wound care plan can be made based on collecting additional wound sample data. Embodiments can further include generating an additional output signature indicative of a condition of the wound sample. The additional output signature can be generated from additional data that can be collected. In further embodiments, the additional output signature can be generated at a later point in time than the output signature. The additional output signature can be used to determine whether the wound is healing, the rate of healing, etc. In embodiments, the output signature and the additional output signature can be used to create a wound healing trajectory metric. The wound healing trajectory metric can be used to evaluate the efficacy of the wound healing plan, whether some or all of the healing plan needs to be adjusted or replaced, etc. The trajectory can be used to choose a treatment option. In embodiments, the wound healing trajectory metric can be used to provide a recommended treatment option. As discussed previously, the recommended treatment option can be adjusted based on collection of additional excitation response wavelengths emitted by the wound sample. Other wound treatment techniques can be included in the recommended treatment option. In embodiments, the recommended treatment option can include a debridement recommendation. The debridement can include removing damaged tissue, necrotic tissue, or foreign matter from the wound, etc.

Various steps in the flow 200 may be changed in order, repeated, omitted, or the like without departing from the disclosed concepts. Various embodiments of the flow 200 can be included in a computer program product embodied in a non-transitory computer readable medium that includes code executable by one or more processors.

Figure 3:
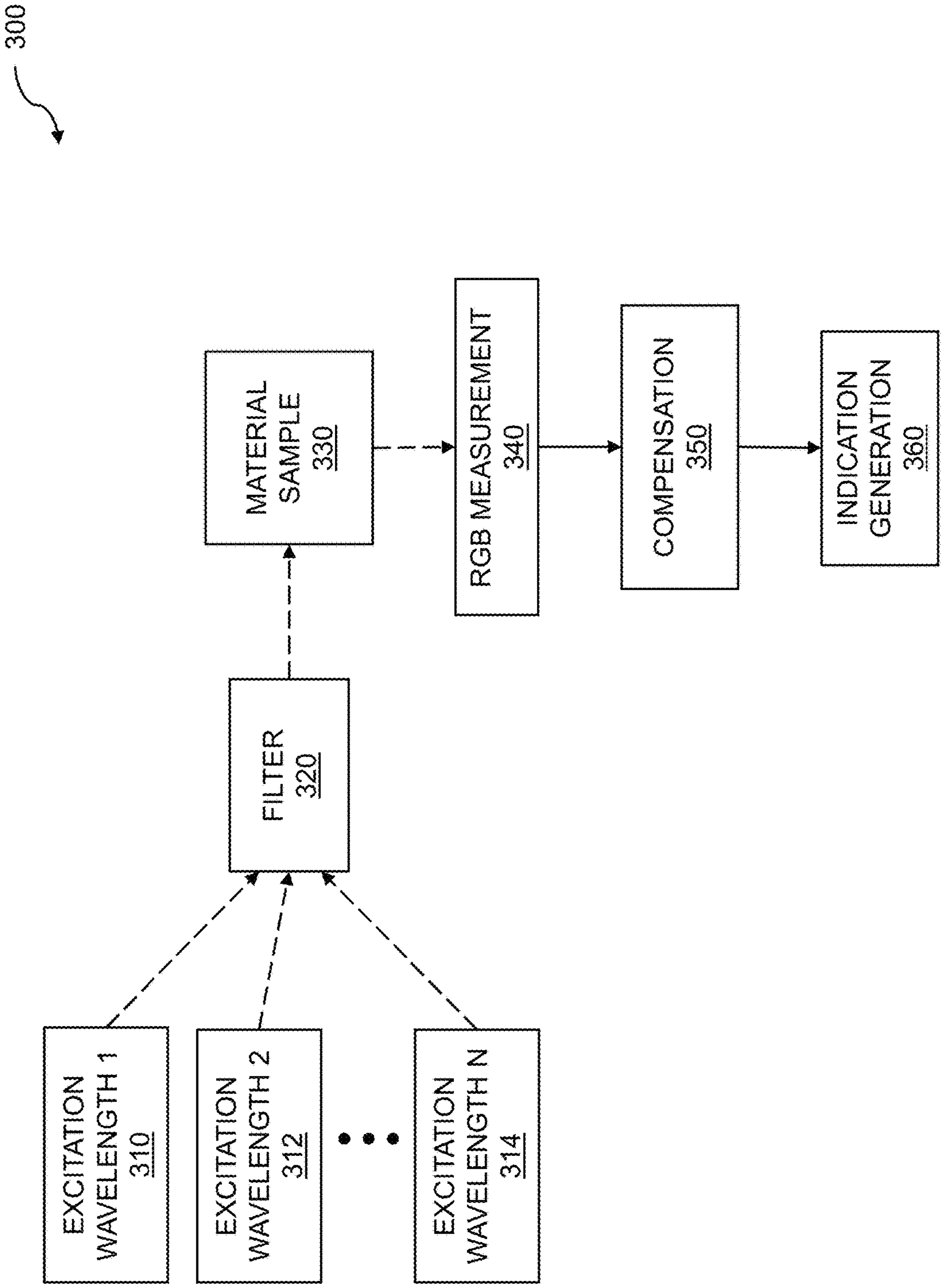
FIG. 3 shows a system block diagram for multispectral sample analysis.

FIG. 3 shows a system block diagram for multispectral sample analysis. A material sample, such as a natural material, a manufactured material, and so on, can be illuminated with a plurality of light spectra. The material sample can include a tissue sample, where the tissue sample is associated with a wound. One or more light spectra within the multispectral light used to illuminate the material sample can cause the material sample to fluoresce. In the system block diagram 300, one or more absorption excitation light wavelengths, such as excitation wavelength 1 310, excitation wavelength 2 312, up to excitation wavelength N 314, are provided to a material sample. The excitation wavelengths can emanate from a single source or from multiple sources, such as from one or more of an incandescent light source, an LED light source, a laser light source, an ultraviolet (UV) light source, an infrared (IR) light source, and so on. The excitation wavelengths can illuminate a sample, and the exciting enables capture of fluorescence characteristics of the material sample. The system block diagram illustrates multispectral sample analysis based on wound care diagnosis with fluorescence signatures. The multispectral light source can be coupled to an electronic device such as a smartphone. The smartphone comprises hardware and software that is associated with wound care image analysis for would diagnosis. A plurality of optical excitation ultraviolet light wavelength bands is scanned on a wound sample. The wound sample exhibits optical spectral characteristics along the light wavelength spectrum. Excitation response wavelengths emitted by the wound sample in response to the plurality of optical excitation ultraviolet light wavelength bands are captured. The capturing is accomplished using an image sensor. Output values of a plurality of pixels of an image from the image sensor are measured. The image represents the excitation response wavelengths captured by the image sensor. The measuring detects optical spectral characteristics of the wound sample, and the optical spectral characteristics are in response to the plurality of optical excitation light wavelength bands. An output signature indicative of a condition of the wound sample is generated. The condition of the wound sample provides a metric of wound monitoring.

The system block diagram 300 can include one or more optical filters 320 on the source side of a material sample 330. That is, the one or more excitation wavelengths 310, 312, and 314 can be conditioned by the one or more optical filters 320 such that the illuminating light from the excitation wavelengths is affected by the filters before it reaches the material sample 330. These filters do not affect the fluorescence emissions of the material sample that are detected by an RGB sensor, based on the illumination of the one or more excitation wavelengths. The filter 320 can be a bandpass filter. The one or more excitation wavelengths, as conditioned by any intervening filters 320, then impinge on a material sample 330, resulting in a fluorescence emission from the sample that is detected by the RGB measurement block 340. Note that before RGB measurement block 340, the system block diagram 300 indicates light transmission, as denoted by the dashed lines among blocks 310, 312, 314, 320, 330, and 340. The output of RGB measurement block 340, as well as the signals between subsequent blocks 350 and 360, are electrical signals, as denoted by the solid lines. Optionally, an additional optical filter (not shown) can be placed between the material sample 330 and the RGB measurement 340. The additional optical filter can be a long-pass filter.

The electrical output of RGB measurement block 340 can be compensated by compensation block 350. Compensation can involve providing a boost or attenuation to electrical signals indicating a certain magnitude of a particular light wavelength in order to counteract sensor differences, ambient lighting differences, excitation wavelength spectra differences, and so on. The compensation block 350 can be adjusted based on various calibration techniques that are performed before or after an actual sample measurement. The output of compensation block 350 can enable generation of an indication 360 of a composition of a material sample. Analysis of the output of compensation block 350 (or directly from RGB measurement block 340) can enable generation of an indication of composition, based on the output of block 350 (or directly from block 340) using various methods such as table lookup, graph comparison, machine learning, human interpretation, signature comparison, and the like.

Figure 4:
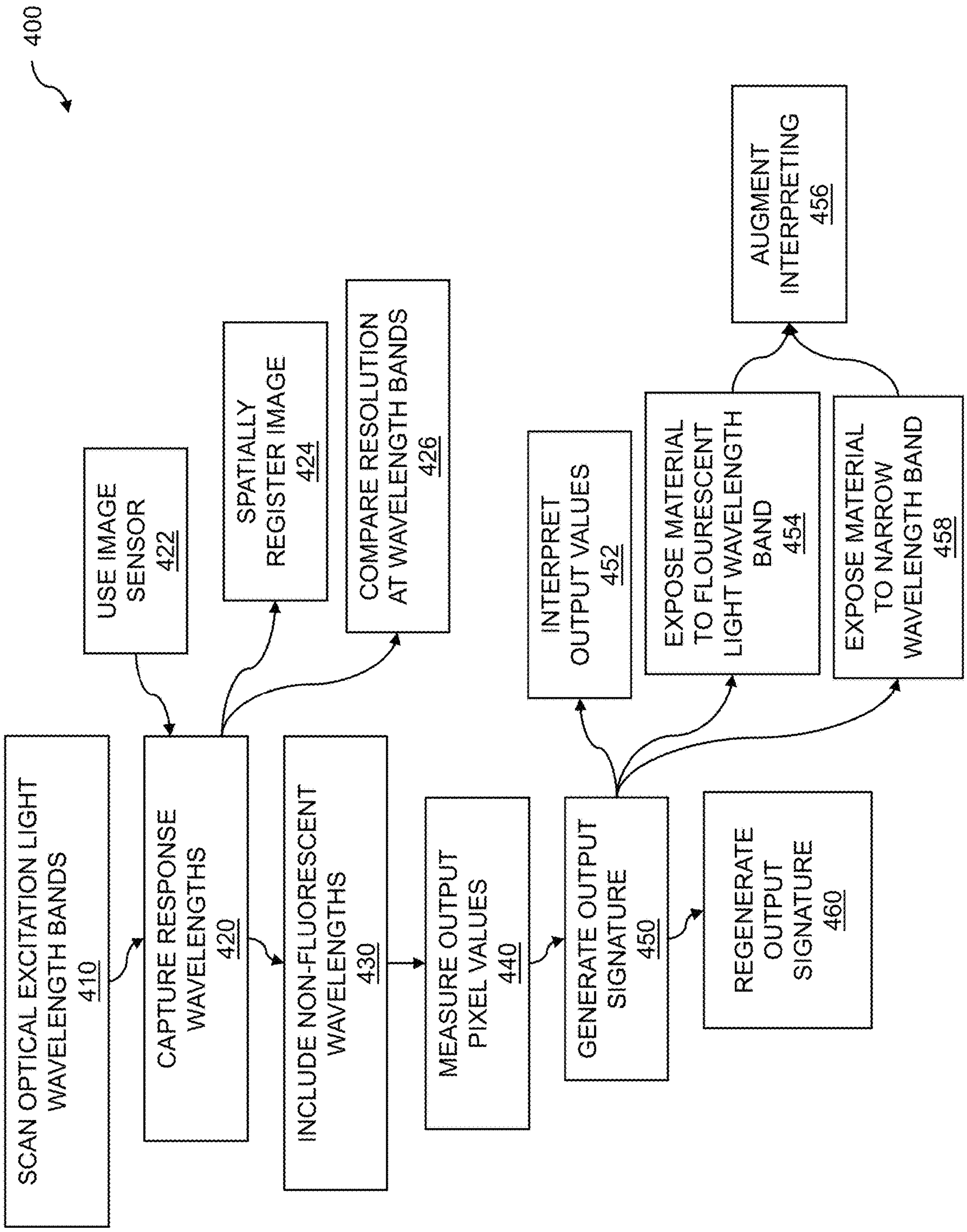
FIG. 4 is a flow diagram for skin diagnostics using optical signatures.

FIG. 4 is a flow diagram for skin diagnostics using optical signatures. The optical signatures can be indicative of a condition of a wound sample. The condition of the wound sample can provide a metric of wound monitoring. The wound monitoring can enable generation of a metric of wound healing. The metric of wound monitoring can distinguish among wound repair, wound regeneration, and wound degeneration. Skin diagnostics enable wound care diagnosis with fluorescence signatures. Optical excitation ultraviolet light wavelength bands are scanned on a wound sample. The wound sample exhibits optical spectral characteristics along the light wavelength spectrum. Excitation response wavelengths are captured, where the excitation response wavelengths are emitted by the wound sample in response to optical excitation ultraviolet light wavelength bands. The capturing is accomplished using an image sensor. Output values of pixels of an image from the image sensor are measured. The image represents the excitation response wavelengths captured by the image sensor. The measuring detects optical spectral characteristics of the wound sample, and the optical spectral characteristics are in response to optical excitation light wavelength bands. An output signature is generated, where the output signature is indicative of a condition of the wound sample. The condition of the wound sample provides a metric of wound monitoring.

The flow 400 includes scanning a plurality of optical excitation light wavelength bands 410 on a material sample. The material sample can include a solid, a liquid, a gel, and so on. In embodiments, the material sample can include cells, tissues, and organs. The material sample can include healthy cells, tissues, and organs or damaged cells, tissues, and organs. In embodiments, the material sample can be from a wound. The material sample that is scanned exhibits optical spectral characteristics along the ultraviolet light wavelength spectrum. The optical spectral characteristics that are exhibited can include fluorescence characteristics. The fluorescence characteristics can occur at the same wavelength as the excitation light or at a different wavelength. The scanned material can exhibit other optical qualities. In embodiments, the plurality of optical excitation light wavelength bands can include one or more non-fluorescent optical excitation light wavelength bands. Based on the type of material that is scanned, the one or more non-fluorescent optical excitation light wavelength bands can coincide with one or more absorption wavelength maximums of selected material constituents (discussed below).

The optical excitation light wavelength bands can include infrared (IR) bands, visible light bands (e.g., red-green-blue, or RGB), long-wavelength IR (LWIR) bands, thermal bands, and so on. In embodiments, a first band of the plurality of optical excitation light wavelength bands can include wavelengths substantially in the range of 325 nm to 375 nm, a second band of the plurality of optical excitation light wavelength bands can include wavelengths substantially in the range of 350 nm to 400 nm, and a third band of the plurality of optical excitation light wavelength bands can include wavelengths substantially in the range of 375 nm to 425 nm. The optical excitation ultraviolet light wavelengths can include 365 nm and 395 nm. The choice of ultraviolet light wavelengths can be based on commercially available ultraviolet light sources. Other bands can also be used. In other embodiments, a fourth band of the plurality of optical excitation light wavelength bands comprises wavelengths substantially in the range of 400 nm to 450 nm. The optical excitation light wavelength bands can include wide bands or narrow bands. In embodiments, the plurality of optical excitation light wavelength bands can include narrow bands substantially at 350 nm, 375 nm, 400 nm, 425 nm, 450 nm, 500 nm, 525 nm, 550 nm, 575 nm, 600 nm, 625 nm, and so on.

The flow 400 includes capturing excitation response wavelengths 420 emitted by the material sample in response to the plurality of optical excitation light wavelength bands. The excitation response wavelengths can include one or more wavelengths. In the flow 400, the capturing is accomplished using an image sensor 422. The image sensor can include an IR sensor, a thermal sensor, and so on. In embodiments, the sensor can include an RGB sensor. The sensor can produce analog or digital output signals. The output values of a sensor, such as an RGB sensor, can include electrical signals, and thus the RGB sensor translates wavelength intensity to an electrical representation by providing three output values: a red output value, a green output value, and a blue output value. These sensors generally demonstrate peak blue sensitivity at 400-475 nm, peak green sensitivity at 475-580 nm, and peak red sensitivity at 580-750 nm. In order to avoid signal contribution from an excitation LED (or other excitation source) that has a long red tail that may be detected by the spectral channels built into the RGB imager, the excitation source may be outfitted with a bandpass filter that prevents crosstalk. Additionally, a long-pass filter placed in front of the RGB sensor further prevents a spurious signal from the excitation LED. The flow 400 further includes spatially registering the image 424 to determine wound features contained in the material sample. In a usage example, the spatially registering the image can include locating a wound, locating a wound edge, locating a wound center, and so on. The flow 400 further includes comparing image resolution 426 at a plurality of narrow optical excitation light wavelength bands. The comparing image resolution at narrow wavelength bands can provide further information associated with the material sample such as a wound sample. In embodiments, the comparing can enable wound depth analysis.

In the flow 400, the plurality of optical excitation light wavelength bands can include one or more non-fluorescent 430 optical excitation light wavelength bands. When scanning a material to determine its constituents, a "negative response" such as a non-fluorescent response can provide useful clues associated with the material. In embodiments, the one or more non-fluorescent optical excitation light wavelength bands can coincide with one or more absorption wavelength maximums of selected material constituents. The flow 400 includes measuring output values 440 of a plurality of pixels of an image from the image sensor. The measuring output values can be based on measuring fluorescence, measuring absorption, and so on. The image from which pixels are measured can represent excitation response wavelengths captured by the image sensor. Further, the measuring output values can include measurements at the absorption wavelength maximums. The measuring detects optical spectral characteristics of the material sample that was scanned. The optical spectral characteristics are measured in response to the plurality of optical excitation light wavelength bands. The measurements can occur at fluorescent wavelengths, absorption wavelengths, and so on. In embodiments, the measurements at the absorption wavelength maximums augment interpreting (discussed below).

The flow 400 includes generating an output signature 450 indicative of composition of the material sample. The output signature can include a variety of indicators and markers. The signature can be based on numerical values, a range of values, ratios, percentages, qualitative evaluations, and so on. In embodiments, the output signature of the wound can include microbe indications, inflammation markers, granulation markers, epithelialization markers, and remodeling markers. The output signature can enable wound care management, where wound care management can include various treatments associated with the wound. In embodiments, the output signature provides a wound state or a wound healing trajectory. The wound state can include a stalled state, a healing state, a non-healing state, an infected state, an inflamed state, a granulating state, or an epithelializing state. The output signature can be indicative of the presence or absence of various constituents within the material sample. In embodiments, the output signature can be indicative of the presence of nicotinamide adenine dinucleotide plus hydrogen (NADH) and flavins. In other embodiments, the output signature can be indicative of the presence of collagen. The NADH, flavins, and collagen can be critical to wound healing. In the flow 400, the output signature is based on interpreting 452 the output values that were measured. The interpreting can be based on output values from the image sensor, and the output values can be indicative of one or more wavelengths. In embodiments, the interpreting can be based on measured wavelengths substantially in the range of 440 nm to 500 nm and 500 nm to 550 nm. Other light wavelengths can also be used. The flow 400 further includes exposing the material sample to a fluorescence excitation light 454 wavelength band. The fluorescence excitation light wavelength band comprises wavelengths substantially in the 315 nm to 375 nm range. In the flow 400, the exposing the material to the fluorescence excitation light wavelength band augments the interpreting 456. The fluorescence excitation light wavelength band can cause further fluorescence of the material. Note also that the measurements at the absorption wavelength maximums (discussed above) can augment the interpreting. In other embodiments, the interpreting can be based on measured wavelengths substantially in the range of 600 nm to 660 nm and 675 nm to 725 nm. The flow 400 further includes exposing the material sample to a narrow fluorescence excitation light wavelength band 458 comprising wavelengths substantially at 400 nm to augment the interpreting 456.

Discussed previously and throughout, the output signature can be generated, where the output signature can be indicative of a condition of the wound sample. Further, the condition of the wound sample can provide a metric of wound monitoring. In embodiments, the metric of wound healing can include an epithelialization metric. The epithelialization metric can be used to describe the degree of epithelialization associated with a wound. Epithelialization describes the formation of epithelium, a thin layer of tissue, in the wound. In embodiments, the epithelialization metric can be based on detecting nicotinamide adenine dinucleotide plus hydrogen (NADH) around the wound. The presence of NADH can indicate healing of a wound, the extent of healing of the wound, and so on. In other embodiments, the epithelialization metric can be further based on detecting a ratio of nicotinamide adenine dinucleotide ($NAD^+$) to nicotinamide adenine dinucleotide plus hydrogen (NADH) around the wound. The $NAD^+$ to NADH ratio can indicate the amount of regulation of an intracellular redox state. The epithelialization metric can be based on further detection. In embodiments, the epithelialization metric can be further based on detecting flavin adenine dinucleotide ($FADH_2$) around the wound. Among other functions, $FADH_2$ can maintain the redox states of cells. In embodiments, the epithelialization metric can be further based on detecting a ratio of flavin adenine dinucleotide (FAD) to flavin adenine dinucleotide plus hydrogen ($FADH_2$) around the wound. In further embodiments, the epithelialization metric can define a spatial halo around a healing perimeter of the wound. The spatial halo around the healing perimeter can be based on a wavelength of light. In embodiments, the spatial halo can include a blue light wavelength ring. The blue light wavelength ring can be captured using an image sensor.

The flow 400 includes regenerating the output signature 460 over time. The regenerating the output signature can be performed based on updated parameter values associated with a wound, changes in fluorescence response, changes in absorption response, and the like. The regenerating the output signature over time can be used to determine whether a wound is healing properly, is healing slowly, is not healing, and so on. In embodiments, the regenerating the output signature over time can inform a wound care treatment plan. The wound care treatment plan can include therapies including medicinal therapies, surgery, and so on.

Various steps in the flow 400 may be changed in order, repeated, omitted, or the like without departing from the disclosed concepts. Various embodiments of the flow 400 can be included in a computer program product embodied in a non-transitory computer readable medium that includes code executable by one or more processors.

Figure 5:
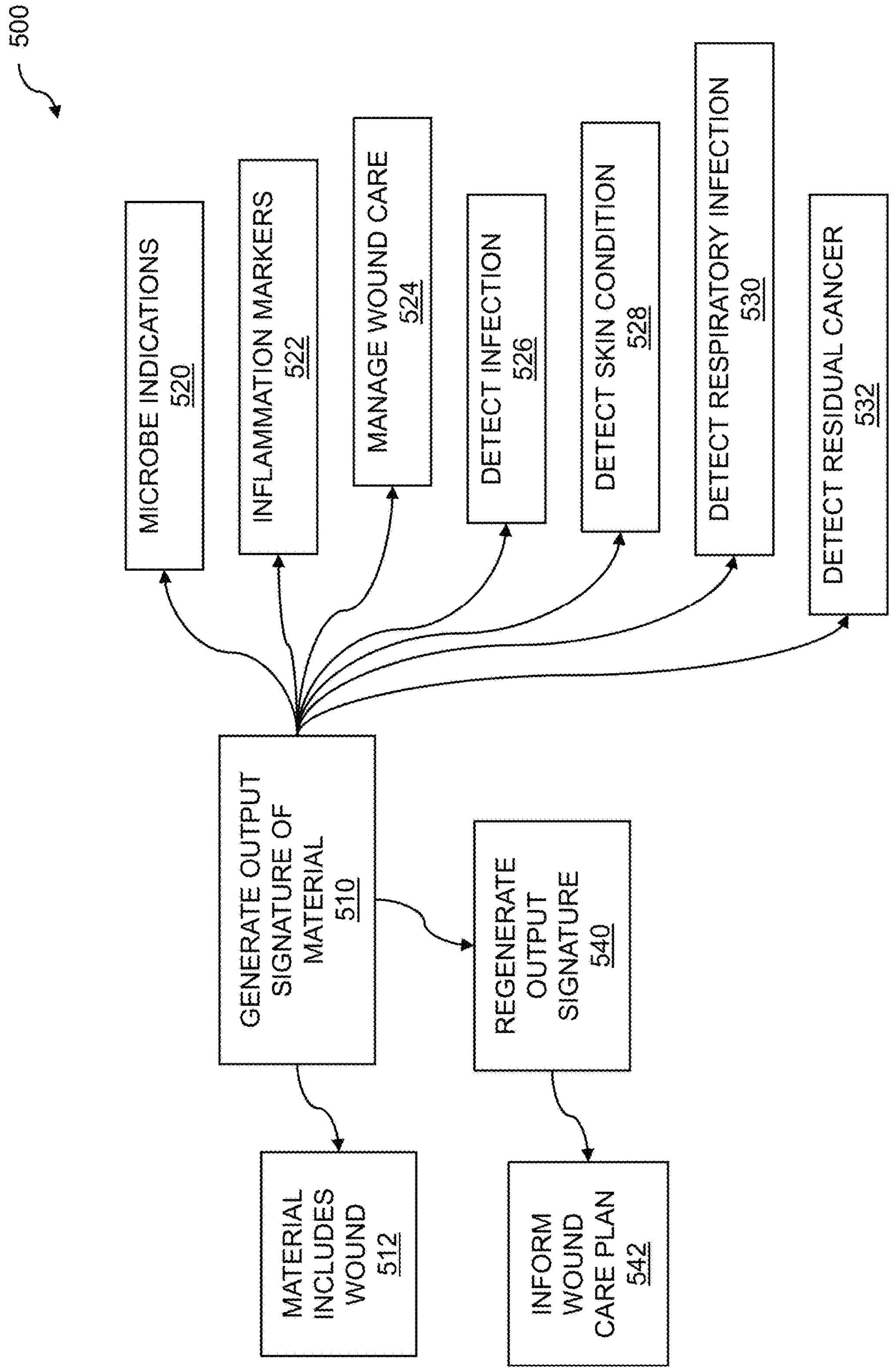
FIG. 5 is a flow diagram for output signature usage.

FIG. 5 is a flow diagram for output signature usage. An output signature that is associated with a material sample such as a wound sample can be generated based on measured excitation responses. The measured excitation responses are based on captured excitation response wavelengths that result from scanning a wound sample with various ultraviolet light wavelength bands. Output signature usage is enabled by wound care diagnosis with fluorescence signatures. A plurality of optical excitation ultraviolet light wavelength bands is scanned on a wound sample. The wound sample can include cells, tissues, and organs. Excitation response wavelengths emitted by the wound sample are captured in response to the plurality of optical excitation ultraviolet light wavelength bands. Output values of a plurality of pixels of an image from the image sensor are measured. An output signature that is indicative of a condition of the wound sample is generated.

The flow 500 includes generating an output signature 510 indicative of composition of the material sample, wherein the output signature is based on interpreting the output values that were measured. The material sample can include a wound sample. The measuring can be based on capturing excitation response wavelengths emitted by the material or wound sample in response to the plurality of optical excitation ultraviolet light wavelength bands. In embodiments, the output signature can describe one or more of temperature, granulation, NADH, water, vascularization, and tissue oxidation. The output signature can indicate the presence of biochemical species such as cells, enzymes, proteins, mediators, chemokines, cytokines, growth factors, proteases, inhibitors, receptors, and so on, as well as healing stages such as hemostasis, infected, inflamed, granulating, epithelializing, remodeling, and so on. The optical excitation light wavelength bands can include a first band of the plurality of optical excitation light wavelength bands comprising wavelengths substantially in the range of 325 nm to 375 nm, a second band of the plurality of optical excitation light wavelength bands comprising wavelengths substantially in the range of 350 nm to 400 nm, and a third band of the plurality of optical excitation light wavelength bands comprising wavelengths substantially in the range of 375 nm to 425 nm. Other optical excitation light wavelength bands may also be used. In a usage example, the optical excitation ultraviolet light wavelengths can include 365 nm and 395 nm. Various material samples can be scanned by the optical excitation light wavelength bands. The material sample can include cells, tissues, and organs. The material sample can include a biopsy sample, a liquid such as exudate, and so on. In the flow 500, the material sample is from a wound 512.

The output signature can include one or more of indications, markers, and so on associated with a wound. In the flow 500, the output signature of the wound includes microbe indications 520. The microbe detection can be used to confirm the presence of an infection and the type of infection. Knowing the species of microbes present in a wound can be used to determine treatment. In the flow 500, the output signature of the wound includes inflammation markers 522. The inflammation markers can detect swelling, elevated temperature, the presence of red lines emanating from the wound, etc. The output signature of the wound further includes granulation markers, epithelialization markers, and remodeling markers. One or more of these markers can be used to characterize a wound, gauge wound healing, and so on. In the flow 500, the output signature enables wound care management 524. The wound care management can include treatment techniques including drug therapies. The drug therapies can include antibiotics to combat microbes, immunosuppression to quell autoimmune conditions, etc. In embodiments, the output signature can provide a wound healing trajectory.

In the flow 500, the output signature enables infection detection 526. Discussed throughout, some wounds can include stalled-healing or nonhealing wounds. These stalled-healing and nonhealing wounds can result from wound parameter imbalances, lack of proteins, and the like. In embodiments, the infection detection can be based on biochrome identification. The biochrome identification can be used to measure parameters associated with a wound, to identify microbes associated with an infection, and so on. In the flow 500, the output signature is used to detect one or more skin conditions 528. Various types of skin conditions can be detected. In embodiments, the skin conditions can include chronic wounds, radiation burns, acne, hives, eczema, psoriasis, cold sores, rosacea, thermal burns, and so on. In the flow 500, the output signature is used to detect respiratory infection 530. A respiratory infection can be associated with the common cold, tonsillitis, laryngitis, sinus infection, and so on. In embodiments, the respiratory infection detection can include influenza detection. Other respiratory infections can be detected. In embodiments, the respiratory infection detection can include COVID-19 detection. In the flow 500, the output signature is used to enable residual cancer detection 532. The residual cancer detection can be performed during surgery, treatment, and so on. In embodiments, the residual cancer detection can occur during oncological surgery. In addition to using the output signature to evaluate chronic wounds or skin conditions, the output signature can be used to evaluate skin cancer.

In embodiments, a metric, such as an epithelialization metric defined previously, can define a spatial halo around a healing perimeter of the wound. The spatial halo can result from the wound sample being scanned with the plurality of optical excitation ultraviolet light wavelength bands. The spatial halo can include a band of light that can be detected using an image sensor. The band of light can include one or more wavelengths or colors of light. In embodiments, the spatial halo can include a blue light wavelength ring.

The flow 500 includes regenerating the output signature 540 over time. The output signature can be regenerated for a variety of purposes such as gauging the depth and extent of a wound, changing the parameter values associated with the wound, and so on. In the flow 500, the regenerating the output signature over time can inform a wound care treatment plan 542. The treatment plan can include a care of the wound such as cleaning and rebandaging the wound, a drug therapy, and so on. In a signature usage example, a wound can be cleaned and redressed daily while a patient is provided with intravenous antibiotics. As the patient heals, the intravenous antibiotics can be replaced by oral antibiotics and the frequency of dressing changes can be reduced. Further, if the regenerating the output signature indicates that the wound is not healing at a sufficient rate, then the treatment protocols for the wound can be adapted, changed, etc.

Various steps in the flow 500 may be changed in order, repeated, omitted, or the like without departing from the disclosed concepts. Various embodiments of the flow 500 can be included in a computer program product embodied in a non-transitory computer readable medium that includes code executable by one or more processors.

Figure 6:
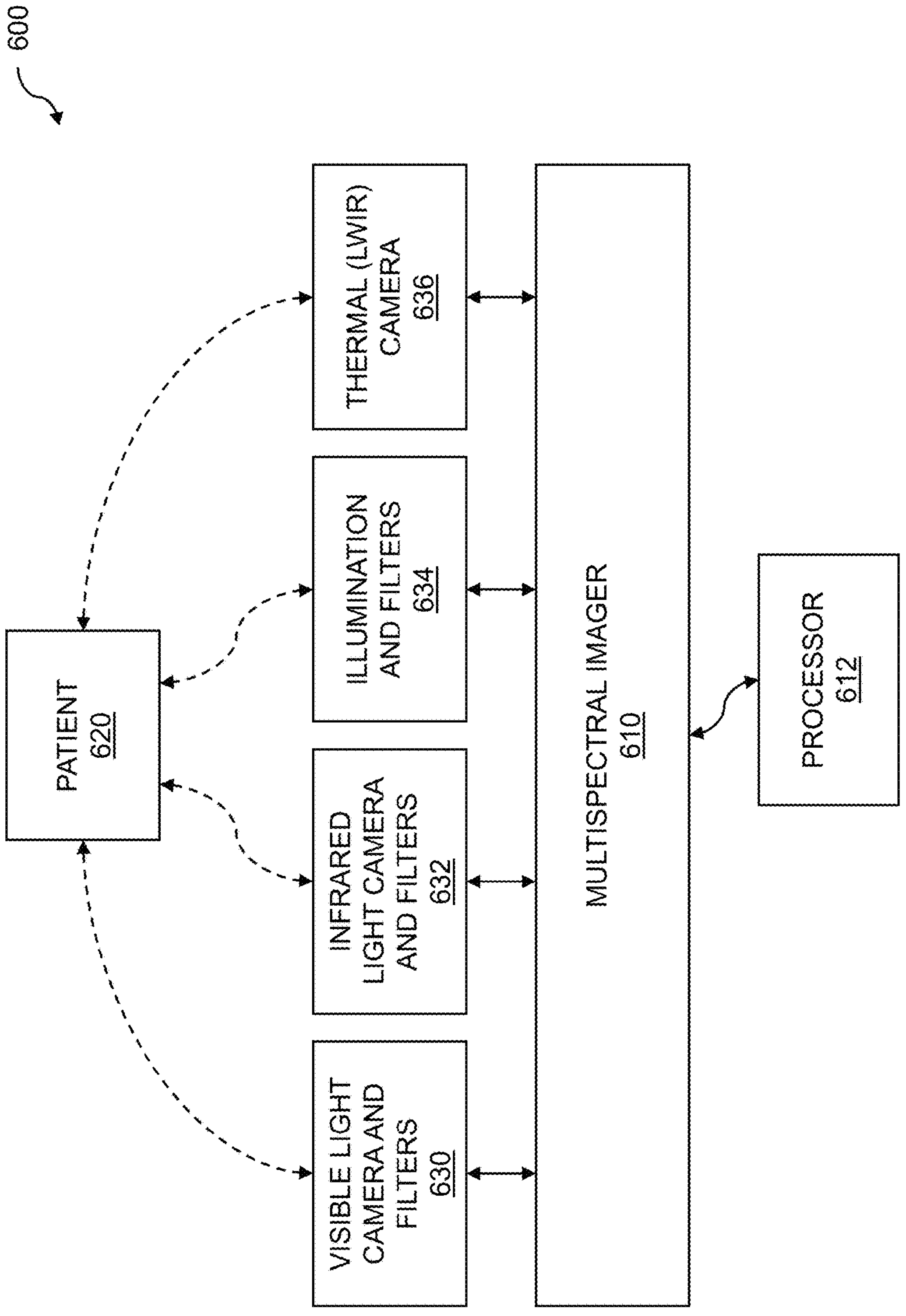
FIG. 6 is a system block diagram for infection locating.

FIG. 6 is a system block diagram for infection locating. A patient can present with one or more indications that can be associated with an infection. Locating the infection can be critical to providing appropriate and timely care to the patient to help them recover from the infection. Locating an infection can be associated with locating a wound or other damage to the skin of the patient. Other infections, such as respiratory infections and COVID-19 infections, and detection of residual cancer, among others, can be harder to locate or identify because the infections or residual cancer are likely not visible. In these and other cases, optical techniques can be applied to infection locating. The infection locating enables wound care diagnostics with fluorescence signatures. Optical excitation ultraviolet light wavelength bands are scanned on a wound sample. The material sample exhibits optical spectral characteristics along the light wavelength spectrum. Excitation response wavelengths emitted by the material sample in response to the optical excitation light wavelength bands are captured using an image sensor. The capturing is accomplished using an image sensor. Output values of a plurality of pixels of an image from the image sensor are measured. The image represents excitation response wavelengths captured by the image sensor. The measuring detects optical spectral characteristics of the wound sample, where the optical spectral characteristics are in response to the optical excitation light wavelength bands. An output signature that is indicative of a condition of the wound sample is generated. The condition of the wound sample provides a metric of wound monitoring.

The system block diagram 600 includes a hyperspectral or multispectral imager 610. The multispectral imager can be based on a handheld component, a mobile cart-based component, and so on. The multispectral imager can receive data from one or more cameras (discussed below) and can measure fluorescence, absorption, and reflection of wound tissue at a variety of optical excitation light wavelength bands. In embodiments, the variety of optical excitation light wavelength bands includes optical excitation ultraviolet light wavelength band. The ultraviolet light wavelength bands can include ultraviolet light produced by standard and commercially available ultraviolet light sources. In a usage example, the optical excitation ultraviolet light wavelengths can include 365 nm and 395 nm. The multispectral imager can be coupled to a processor 612. The processor can control illumination sources, filters, cameras, sensors, and so on. The processor or processors can execute code, where the code can perform various operations associated with the infection detection. The code can include code for control, image processing, data analysis, etc. The processor can be used to isolate signals from biochromes associated with infection. The signal isolation from biochromes associated with infection can be accomplished by scanning a material sample with one or more optical excitation light wavelength bands. The excitation wavelength can be held constant while one or more signals are collected from progressively longer wavelength emission bands. In embodiments, the multispectral imager can collect and isolate signals associated with nicotinamide adenine dinucleotide plus hydrogen (NADH) and flavins by collecting 440-500 and 500-550 nm emission photons, respectively, and scanning excitation (325-375 nm, 350-400 nm, 375-425 nm, 400-450 nm).

The multispectral imager can be used to locate infection associated with a patient 620. The infection can include an infection associated with a material sample such as skin, a respiratory infection, a particular infection such as a COVID-19 infection, residual cancer detection, and so on. The infection location can be accomplished using a handheld scanner, a cart-based scanner, and the like, as discussed throughout. The multispectral imager can be coupled to a variety of components including illumination sources, filters, cameras, and so on. The system block diagram 600 includes a visible light camera and filters 630. The camera can include an image sensor, where the image sensor can detect wavelengths within the visible light band. The visible light band can include one or more wavelengths between 380 nm and 700 nm. The visible light filters can include one or more of a red filter, a green filter, a blue filter, etc. The system block diagram 600 includes an infrared light camera and filters 632. The infrared camera, which can be based on an infrared image sensor, can detect wavelengths within the infrared band. The infrared band can include wavelengths between 780 nm and 1 mm. The infrared filters can be used to capture or isolate one or more wavelength bands within the infrared band. The system block diagram 600 can include illumination and filters 634. The illumination can be based on a plurality of optical excitation light wavelength bands, where the light wavelength bands can include visible light, IR light, long wavelength infrared (LWIR) light, and so on. The filters can include one or more filters which can be used to provide specific optical excitation light wavelengths. The system block diagram 600 can include a thermal (LWIR) camera 636. As noted throughout, detection of infection can include detection of elevated temperature or a "hot spot" on a material sample such as a skin sample. In the system block diagram 600, the illumination and filters can be used to provide a plurality of optical excitation light wavelength bands that can be scanned on a material sample. The material sample, such as a skin sample, a body part, a limb, exudate, and so on, can be associated with the patient 620.

Figure 7:
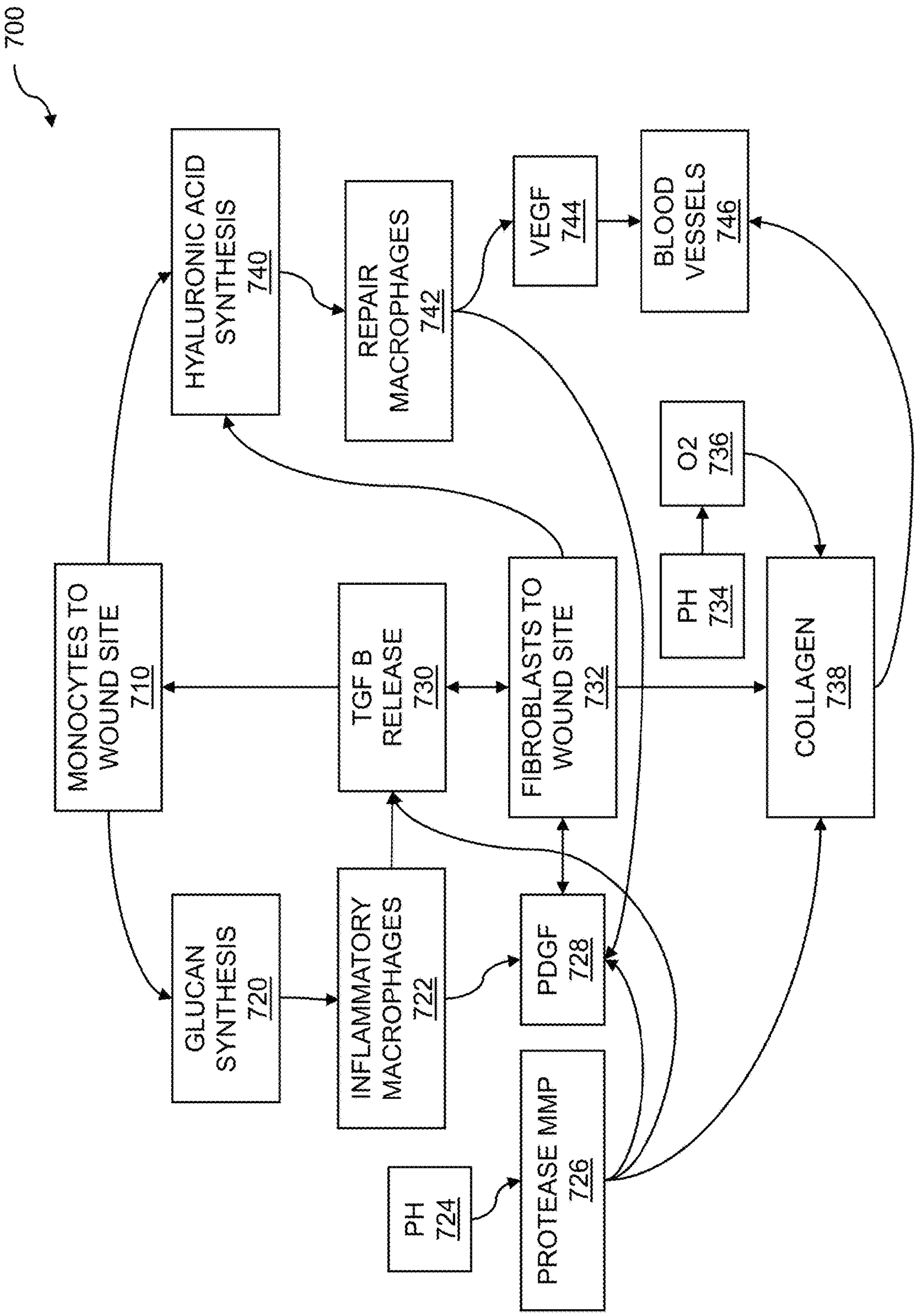
FIG. 7 is a system block diagram for dermis healing.

FIG. 7 is a system block diagram for dermis healing. A dermis healing assessment can be based on performing wound healing measurements, where the wound healing measurements can be based on exudate analysis. While some chronic wounds may not be infected, they can remain chronic or can be slow to heal. The slow healing can be caused by a variety of factors such as poor blood supply, elevated protease activity, and so on. The latter can destroy proteinaccous signals that are required for healing. The dermis healing can be improved by wound care diagnosis with fluorescence signatures. Optical excitation ultraviolet light wavelength bands are scanned on a material sample. Excitation response wavelengths emitted by the wound sample are captured in response to the optical excitation ultraviolet light wavelength bands. The capturing is accomplished using an image sensor. Output values of a plurality of pixels of an image from the image sensor are measured, where the image represents excitation response wavelengths captured by the image sensor. An output signature indicative of a condition of the wound sample is generated. The condition of the wound sample provides a metric of wound monitoring.

In order to determine a treatment that is best suited to a wound such as an infected wound, a variety of factors can be determined. These factors, which in embodiments can include ten to twenty factors, can work together to promote healing. Typically, no one treatment addresses all of the factors. The system block diagram 700 shows a basic overview of key factors associated with a wound, signaling pathways, and immigrant and resident dermal cells that can coordinate reparative and regenerative responses of wound healing. A wound image can be analyzed, and wound exudate can be analyzed to determine one or more biomarkers. The wound exudate can be obtained from a bandage associated with a patient, beneath a film, present in a negative pressure system, and so on. The wound exudate can be analyzed in a laboratory, a bed-side assay, etc. In embodiments, an assay array can be used to detect molecules of interest to determine wound healing. The molecules of interest can include key saccharides and proteins such as glucan, IL1B, IL6, TNF, pH, MMP1, MMP2, MMP8, MMP9, MMP13, TGFB1, Angiopoietin-1, Angiopoietin-2, Angiogenin, endostatin, CD105, CD31, GM-CSF, TIMP1-4, hyaluronic acid, Collagens I/III/IV, IL10, VEGF, HB-EGF, EGF, PDGF, and so on.

In the system block diagram 700, an individual's insult and resulting innate and adaptive immune responses can stimulate microvascular leakage, signaling neutrophils and monocyte/macrophages to a wound site 710. Glucan synthesis 720 can occur and support inflammatory macrophages 722. In addition, hyaluronic acid synthesis 740 can occur and repair macrophages 742. Transforming growth factor beta (TGF B) can be released 730 from repair macrophages 730 and affect fibroblasts 732 at the wound site. Platelets, fibroblasts, and vascular cells contribute to platelet-derived growth factor (PDGF) 728 and several other growth factor products, e.g., FGF, VEGF, etc. Fibroblasts, vascular cells, and macrophages produce protease matrix metalloproteinases (MMPs) 726, which are affected by the local pH 724. The fibroblasts and vascular cells can also influence hyaluronic acid synthesis 740 and the production of collagen 738. The pH 734 can also affect microbial proliferation, oxygen (O2) 736 levels, which have a bearing on collagen synthesis, and basement membrane assembly (when pH is optimal for healing). The collagen 738 affects blood vessels 746 as well. Repair macrophages 742 can in turn affect both PDGF 728 and vascular endothelial growth factor (VEGF) 744. Thus, even the basic overview dermis healing system block diagram 700 shows how complex the process is.

Figure 8:
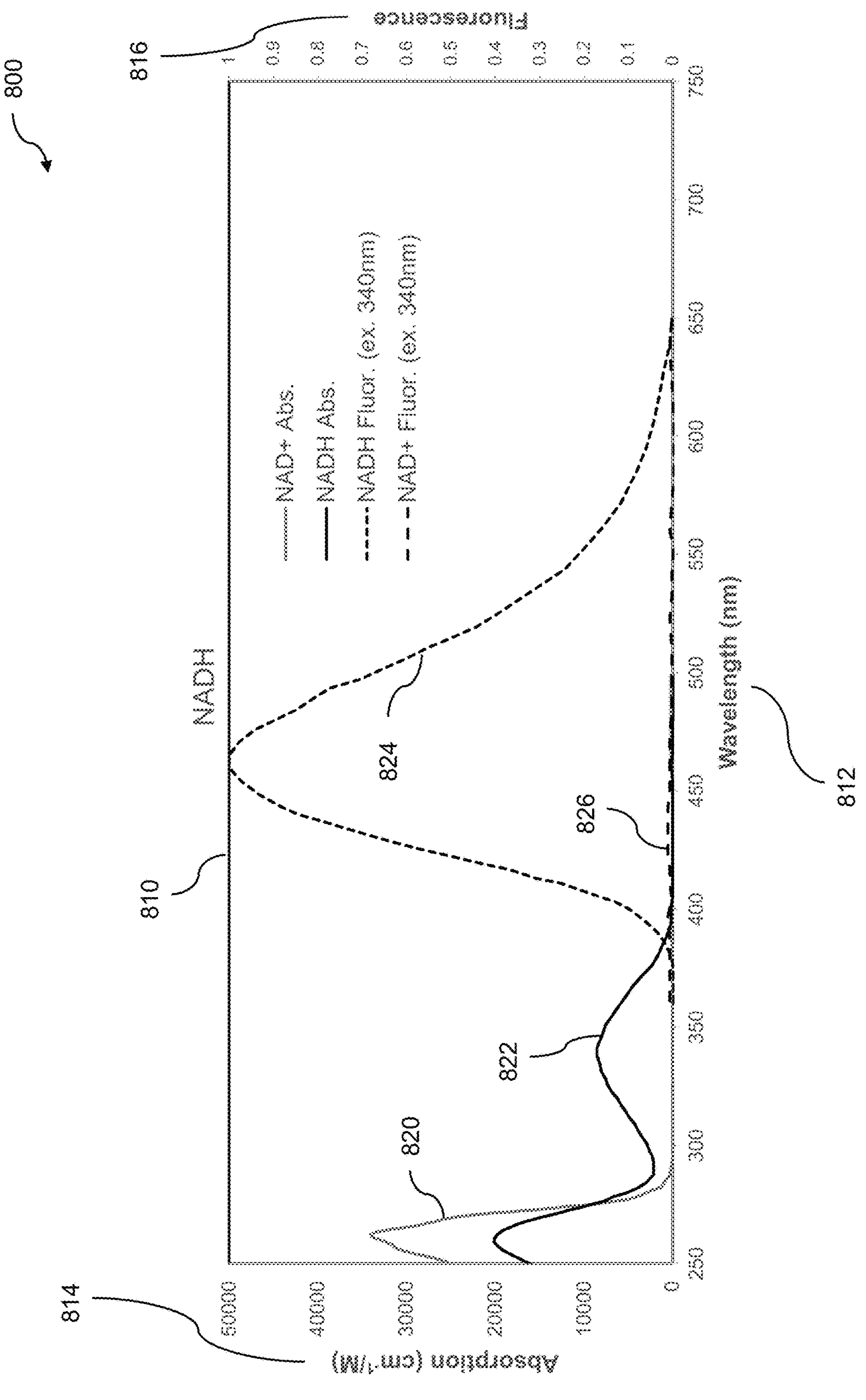
FIG. 8 is a graph illustrating $NAD^+$ and NADH absorption and emission/fluorescence.

FIG. 8 is a graph illustrating $NAD^+$ and NADH absorption and emission/fluorescence. Described previously and throughout, optical excitation light wavelength bands can be scanned onto a material sample such as a wound sample. The optical excitation light wavelength bands include optical excitation ultraviolet light wavelength bands. The ultraviolet wavelength bands that are scanned can be provided by one or more ultraviolet light (UV) sources. The UV light sources can include incandescent sources, LED sources, laser sources, and so on. The UV light sources can include commercially available sources that are chosen based on their size, cost, availability, utility for analyzing wound samples, and the like. The UV light sources can be chosen based on their absorption and emission/fluorescence characteristics when scanned onto a wound sample. The absorption and emission/fluorescence characteristics can include one or more fluorescence signatures. The one or more fluorescence signatures enable wound care diagnosis.

A plurality of optical excitation ultraviolet light wavelength bands is scanned on a wound sample. The wound sample exhibits optical spectral characteristics along the light wavelength spectrum. Excitation response wavelengths are captured, where the response wavelengths are emitted by the wound sample in response to the plurality of optical excitation ultraviolet light wavelength bands. The capturing is accomplished using an image sensor. Output values of a plurality of pixels of an image from the image sensor are measured. The image represents the excitation response wavelengths captured by the image sensor. The measuring detects optical spectral characteristics of the wound sample, and the optical spectral characteristics are in response to the plurality of optical excitation light wavelength bands. An output signature that is indicative of a condition of the wound sample is generated. The condition of the wound sample provides a metric of wound monitoring.

In the illustration 800, a graph 810 is shown that illustrates oxidized nicotinamide adenine dinucleotide ($NAD^+$) and reduced nicotinamide adenine dinucleotide (NADH) absorption and emission/fluorescence around a wound. The graph 810 shows an x-axis of wavelengths in nanometers 812, a left y-axis of absorption intensity in arbitrary units 814, and a right y-axis of relative fluorescence 816. Note that a light wavelength such as an ultraviolet light emission at a certain wavelength can cause fluorescence at a different wavelength by the wound sample. The excitation response wavelengths based on the plurality of excitation wavelengths can include a fluorescence signature for the wound sample. An absorption signature for a substance of interest in the wound sample can be determined using spectrophotometry. The wound sample can be analyzed to provide a metric of wound monitoring. In embodiments, the metric of wound healing can include an epithelialization metric. Discussed above, the epithelialization metric can be based on detecting one or more factors around the wound from which the wound sample was obtained. The factors can be obtained by detecting $NAD^+$, NADH, FAD, and $FADH_2$ around the wound. Ratios can include a ratio of $NAD^+$ to NADH and/or FAD to $FADH_2$ around the wound. Around the wound can include wound edges, wound perimeters, wound centers, wound areas, periwound regions, and so on.

The graph 810 includes absorption signatures for $NAD^+$ 820 and NADH 822. It can be seen that while $NAD^+$ 820 and NADH 822 have absorption peaks around 270 nm, NADH also has a localized peak at around 340 nm. Using 340 nm as an excitation wavelength produces a large fluorescence response peak for NADH 824 at about 460 nm, while the $NAD^+$ fluorescence response 826 exhibits almost no fluorescence. The optical excitation ultraviolet wavelength band (s) can be chosen for detection of $NAD^+$ and/or NADH. The choices of optical excitation ultraviolet wavelength bands can be based on emitter cost, availability, commercial availability versus custom availability, and so on. In embodiments, the $NAD^+$ and/or NADH optical excitation ultraviolet light wavelength bands can include wavelengths substantially in the range of 325 nm to 400 nm. One or more wavelengths can be provided. In a usage example, the optical excitation ultraviolet wavelength can include substantially a 340 nm excitation wavelength. Other wavelengths may be used, however, such as a substantially 365 nm wavelength, which may be a wavelength whose emitter is readily available, inexpensively available, useful for other biochromes of interest, and so on. An additional optical excitation ultraviolet light wavelength can be present. In the case of considering a ratio of $NAD^+$ to NADH fluorescence, the fluorescence from NADH excited by a 340 nm wavelength is ~100× larger than the $NAD^+$ fluorescence. Therefore, measuring a fluorescence signal at 460 nm after excitation at 340 nm can be a useful indicator of metabolic state.

Figure 9:
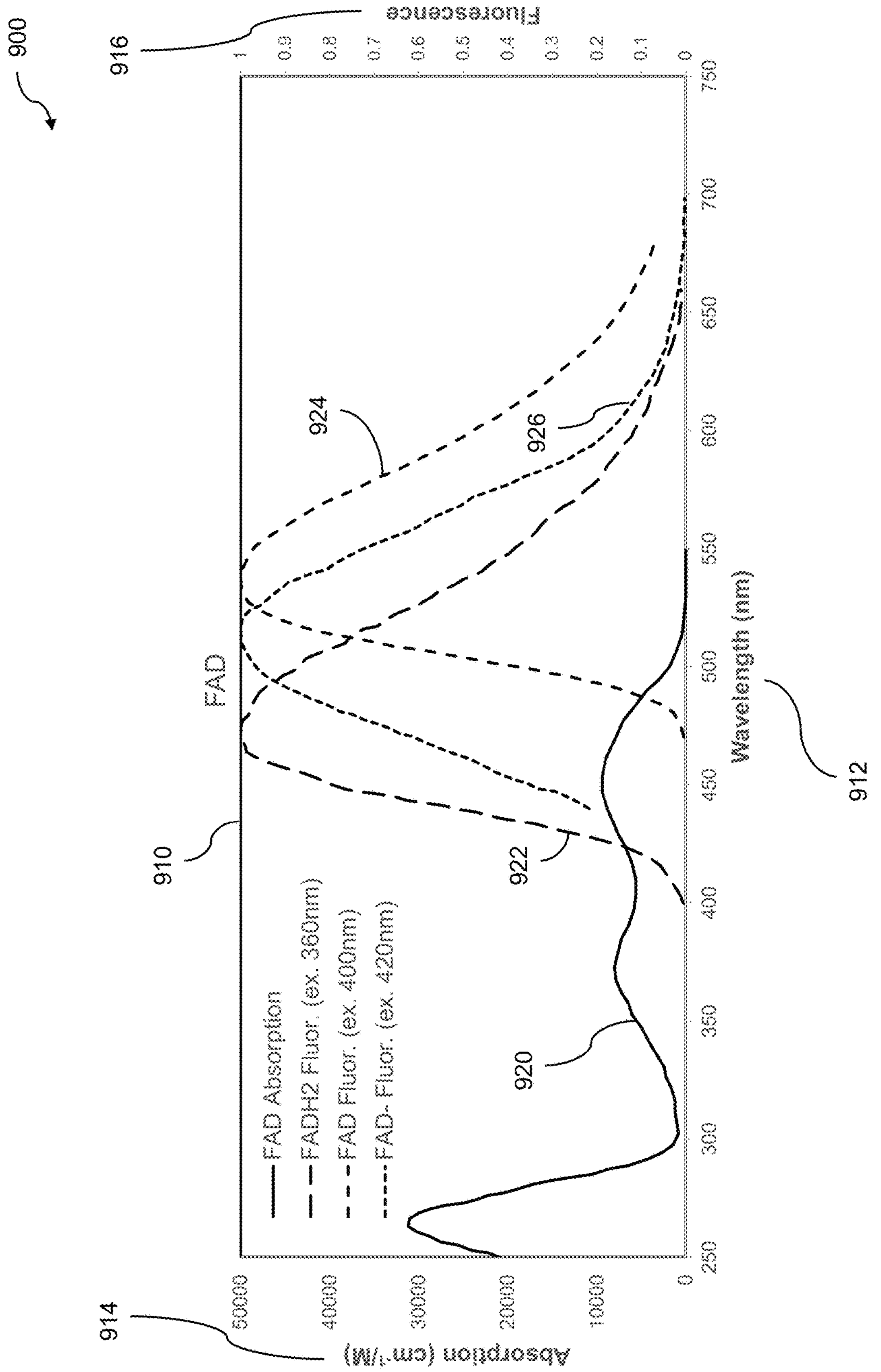
FIG. 9 is a graph illustrating FAD and $FADH_2$ absorption and emission/fluorescence.

FIG. 9 is a graph illustrating FAD and $FADH_2$ absorption and emission/fluorescence. Described previously and throughout, optical excitation light wavelength bands can be scanned onto a material sample such as a wound sample. The optical excitation light wavelength bands include optical excitation ultraviolet light wavelength bands. The ultraviolet wavelength bands that are scanned can be provided by one or more ultraviolet light (UV) sources. The UV light sources can include incandescent sources, LED sources, laser sources, and so on. The UV light sources can include commercially available sources that are chosen based on their size, cost, availability, utility for analyzing wound samples, and the like. The UV light sources can be chosen based on their absorption and emission/fluorescence characteristics when scanned onto a wound sample. The absorption and emission/fluorescence characteristics can include one or more fluorescence signatures. The one or more fluorescence signatures enable wound care diagnosis.

A plurality of optical excitation ultraviolet light wavelength bands is scanned on a wound sample. The wound sample exhibits optical spectral characteristics along the light wavelength spectrum. Excitation response wavelengths are captured, where the response wavelengths are emitted by the wound sample in response to the plurality of optical excitation ultraviolet light wavelength bands. The capturing is accomplished using an image sensor. Output values of a plurality of pixels of an image from the image sensor are measured. The image represents the excitation response wavelengths captured by the image sensor. The measuring detects optical spectral characteristics of the wound sample, and the optical spectral characteristics are in response to the plurality of optical excitation light wavelength bands. An output signature that is indicative of a condition of the wound sample is generated. The condition of the wound sample provides a metric of wound monitoring.

In the illustration 900, a graph 910 is shown that illustrates oxidized flavin adenine dinucleotide (FAD) and reduced flavin adenine dinucleotide ($FADH_2$) absorption and emission/fluorescence around a wound. The graph 910 shows an x-axis of wavelengths in nanometers 912, a left y-axis of absorption intensity in arbitrary units 914, and a right y-axis of relative fluorescence 916. Note that a light wavelength such as an ultraviolet light emission at a certain wavelength can cause fluorescence at a different wavelength by the wound sample. The excitation response wavelengths based on the plurality of excitation wavelengths can include a fluorescence signature for the wound sample. An absorption signature for a substance of interest in the wound sample can be determined using spectrophotometry. The wound sample can be analyzed to provide a metric of wound monitoring. In embodiments, the metric of wound healing can include an epithelialization metric. Discussed above, the epithelialization metric can be based on detecting one or more factors around the wound from which the wound sample was obtained. The factors can be obtained by detecting $NAD^+$, NADH, FAD, and $FADH_2$ around the wound. Ratios can include a ratio of $NAD^+$ to NADH and/or FAD to $FADH_2$ around the wound. Around the wound can include wound edges, wound perimeters, wound centers, wound areas, periwound regions, and so on.

The graph 910 includes an absorption signature for FAD 920. It can be seen that while FAD 920 has an absorption peak around 270 nm, FAD also has localized peaks at around 370 nm and 450 nm. Using 400 nm as an excitation wavelength produces a large fluorescence response peak for FAD 924 at about 540 nm, while using 420 nm as an excitation wavelength produces a large fluorescence response peak for FAD 926 at about 520 nm. Furthermore, using 360 nm as an excitation wavelength produces a large fluorescence response peak for $FADH_2$ 922 at about 470 nm. The optical excitation ultraviolet wavelength band(s) can be chosen for optimized detection of FAD and/or $FADH_2$ and/or $NAD^+$ and/or NADH. The choices of optical excitation ultraviolet wavelength bands can be based on emitter cost, availability, commercial availability versus custom availability, and so on. In embodiments, the FAD and/or $FADH_2$ optical excitation ultraviolet light wavelength bands can include wavelengths substantially in the range of 325 nm to 400 nm. One or more wavelengths can be provided. In a usage example, the optical excitation ultraviolet wavelength can include substantially a 360 nm excitation wavelength. Other wavelengths may be used, however, which may be a wavelength whose emitter is readily available, inexpensively available, useful for other biochromes of interest, able to be combined for detection of other biochromes, and so on. An additional optical excitation ultraviolet light wavelength can be present. In the case of considering a ratio of FAD to $FADH_2$ fluorescence, the fluorescence from FAD excited by a 400 nm wavelength produces a very different peak from the fluorescence of $FADH_2$ excited by a 360 nm wavelength (540 nm vs. 470 nm). Therefore, measuring a fluorescence signal at 470 nm after excitation at 360 nm can be a useful indicator of metabolic state.

Figure 10:
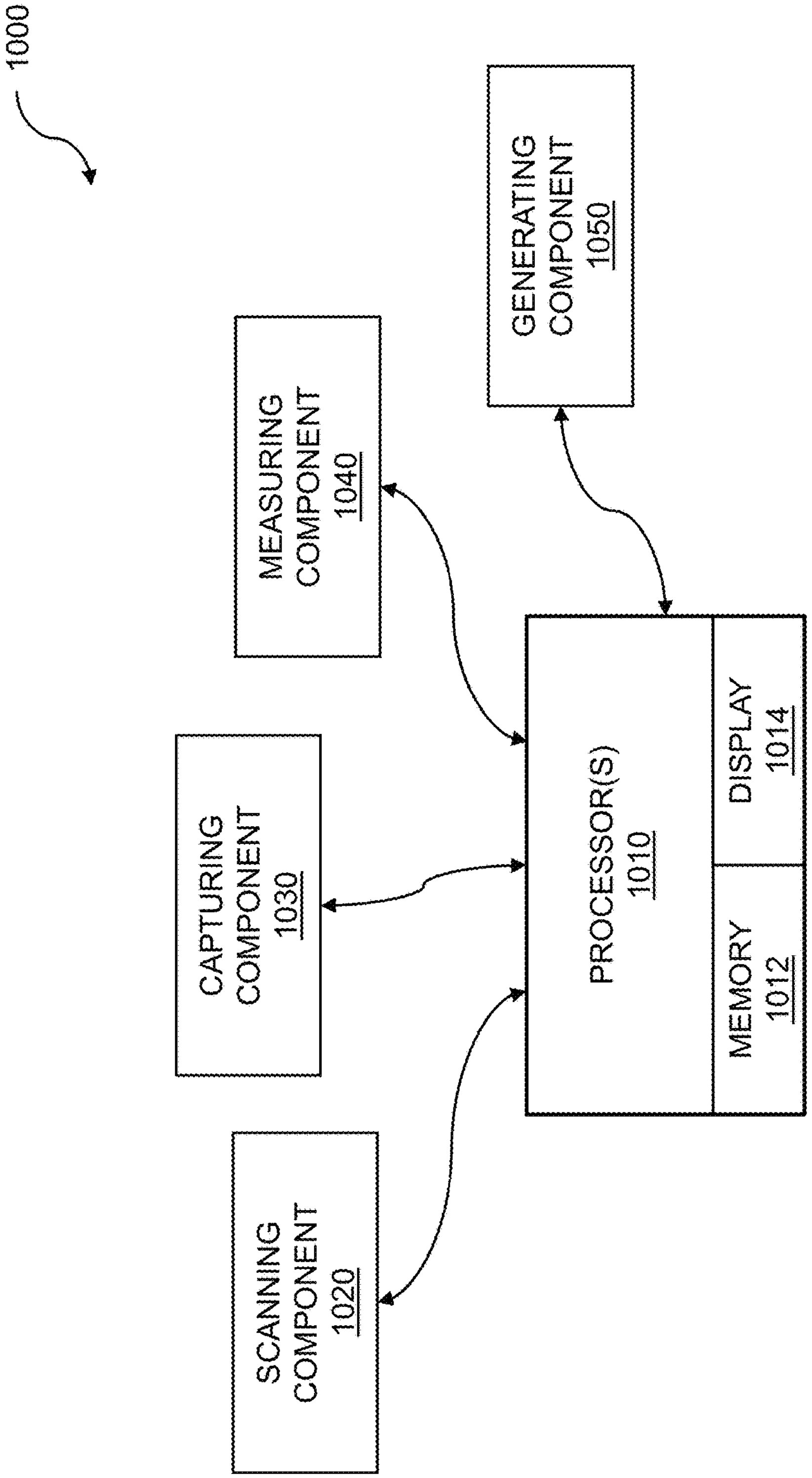
FIG. 10 is a system diagram for wound care diagnosis with fluorescence signatures.

FIG. 10 is a system diagram for wound care diagnosis with fluorescence signatures. The system 1000 can include one or more processors 1010, which are coupled to a memory 1012 which stores instructions. The system 1000 can further include a display 1014 coupled to the one or more processors 1010 for displaying data, indications of sample analysis, illumination signatures, wound centers and perimeters, spatial halos, directions, input requests, control options, excitation wavelengths, filter options, compensation options, data forwarding options, and so on. Embodiments of the system 1000 comprise a computer system for wound care diagnosis comprising: one or more processors 1010 that are coupled to the memory 1012 which stores instructions, wherein the one or more processors, when executing the instructions which are stored, are configured to: scan a plurality of optical excitation ultraviolet light wavelength bands on a wound sample, wherein the wound sample exhibits optical spectral characteristics along the light wavelength spectrum; capture excitation response wavelengths emitted by the wound sample in response to the plurality of optical excitation ultraviolet light wavelength bands, wherein the capturing is accomplished using an image sensor; measure output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generate an output signature indicative of a condition of the wound sample, wherein the condition of the wound sample provides a metric of wound monitoring.

The system 1000 can include a scanning component 1020. The scanning component 1020 can be used to scan a plurality of optical excitation ultraviolet light wavelength bands on a wound sample, where the wound sample exhibits optical spectral characteristics along the light wavelength spectrum. The wound sample can comprise one or more materials, samples, and so on. In embodiments, the wound sample can include cells, tissues, and organs. The wound sample can be collected from a variety of cells, tissues, and organs associated with a patient. In a usage example, the material sample can include healthy tissue, damaged tissue, and so on. The optical excitation light wavelength bands can be provided by various sources including an incandescent light source, an LED light source, a laser light source, and so on. The light source or sources can emit a narrow spectrum of light at primarily one wavelength, at primarily two or more wavelengths, across a broad spectrum of multiple wavelengths, in the visible spectrum, in the infrared spectrum, in the ultraviolet spectrum, and so on. The excitation wavelengths can be targeted towards material sample fluorescence or material sample absorption. A fluorescence excitation light wavelength signal can have a wavelength which is less than a wavelength of the RGB light wavelength spectrum. The wavelength less than a wavelength of the RGB light wavelength spectrum can be substantially between 200 nm and 450 nm. The wavelength bands can include a first band of the plurality of optical excitation light wavelength bands comprising wavelengths substantially in the range of 325 nm to 375 nm, a second band of the plurality of optical excitation light wavelength bands comprising wavelengths substantially in the range of 350 nm to 400 nm, and a third band of the plurality of optical excitation light wavelength bands comprising wavelengths substantially in the range of 375 nm to 425 nm. In embodiments, a fourth band of the plurality of optical excitation light wavelength bands comprises wavelengths substantially in the range of 400 nm to 450 nm. In a usage example, two excitation wavelengths can be used, where the two excitation wavelengths can include 365 nm and 395 nm.

The system 1000 can include a capturing component 1030. The capturing component 1030 can capture excitation response wavelengths emitted by the wound sample in response to the plurality of optical excitation ultraviolet light wavelength bands. The capturing is accomplished using an image sensor. The image sensor can include an RGB sensor, an infrared (IR) sensor, a long wavelength IR (LWIR) sensor, an ultraviolet sensor, and so on. In embodiments, a broadband sensor can be used with one or more filters. In a usage example, the broadband sensor can be used with filters for ultraviolet light wavelengths such as a filter for 365 nm and a second filter for 395 nm. The capturing an illumination signature can be initiated by a series of flashes from an external light source. The light associated with the flashes can include one or more light wavelengths. The one or more light wavelengths can be included in each flash, in different flashes, and the like. The capturing an excitation response can be initiated using wireless communication to an external light source. The wireless communication can be based on a communication standard such as Wi-Fi™, Bluetooth™, Zigbee™, etc.

The system 1000 can include a measuring component 1040. The measuring component 1040 can measure output values of a plurality of pixels of an image from the image sensor. The measuring component can provide a digital or analog signal output related to output values of the image from the image sensor. The image represents the excitation response wavelengths captured by the image sensor. The measuring can detect optical spectral characteristics of the wound sample. The optical spectral characteristics can include fluorescence, absorption, and so on. The optical spectral characteristics can be in response to the plurality of optical excitation light wavelength bands. The plurality of optical excitation light wavelength bands can include narrow bands substantially at 350 nm, 375 nm, 400 nm, 425 nm, 450 nm, 500 nm, 525 nm, 550 nm, 575 nm, 600 nm, 625 nm, and so on. In embodiments, the excitation response wavelengths comprise wavelengths substantially in a range of 440 nm to 500 nm and 500 nm to 550 nm. The output of the measuring can be processed using various signal processing techniques. For example, the measuring component output can be compensated to account for naturally occurring manufacturing differences associated with a sensor by completing a calibration step before the material sample is analyzed.

The system 1000 can include a generating component 1050. The generating component 1050 can generate an output signature indicative of a condition of the wound sample. The output signature can be based on interpreting the output values that were measured. The output signature can be indicative of the presence or absence of cells, proteins, and so on. In embodiments, the output signature can be indicative of the presence of nicotinamide adenine dinucleotide plus hydrogen (NADH) and flavins. The interpreting used to generate the output signature can be based on measured wavelengths, where the measured wavelengths can be associated with fluorescence, absorption, and so on. In other embodiments, the output signature can be indicative of the presence of collagen, the presence of porphyrins, and the like. When the output signature is generated for a material sample associated with a wound, the output signature can include microbe indications, inflammation markers, granulation markers, epithelialization markers, and remodeling markers. The output signature can be used for a variety of purposes including wound care management, providing a wound healing trajectory, detecting infection, etc. A detected infection can include a respiratory infection. Further embodiments include regenerating the output signature over time. The output signature can be regenerated based on new parameter values which can be obtained for scanning an additional material sample. In embodiments, the regenerating the output signature over time can inform a wound care treatment plan. The output signature, the regenerated output signature, and so on can be useful for enabling medical evaluation such as skin assessment; wound assessment; wound assessment over time; treatment planning for wound care; infection detection; biochrome identification; respiratory infection detection; influenza detection; COVID-19 detection; residual cancer detection; oncological surgery residual cancer detection; oral hygiene detection such as detecting plaques, gingivitis, and other dental abnormalities; and so on. The generated and regenerated signatures can have applications in food recognition, food quality assessment, or food safety evaluation, detecting food adulteration, monitoring progression of fermentation, optimizing agricultural yield, and enabling field sobriety evaluation of individuals, to name just a few.

In other embodiments, the metric of wound healing comprises an epithelialization metric. The analysis can include identifying epithelialization within the wound sample. Epithelialization can include a migration of epithelial cells upward to repair a damaged or wounded area of the body such as a skin wound. The identifying epithelization can indicate a level of healing of a skin wound. In embodiments, the epithelialization metric can be based on detecting nicotinamide adenine dinucleotide plus hydrogen (NADH) around the wound. The epithelialization metric can be based on a ratio. In embodiments, the epithelialization metric can be further based on detecting a ratio of nicotinamide adenine dinucleotide (NAD+) to nicotinamide adenine dinucleotide plus hydrogen (NADH) around the wound. The epithelialization metric can be based on further detecting. In embodiments, the epithelialization metric can be further based on detecting flavin adenine dinucleotide ($FADH_2$) around the wound. The epithelialization can be based on a further ratio. In embodiments, the epithelialization metric is further based on detecting a ratio of flavin adenine dinucleotide (FAD) to flavin adenine dinucleotide plus hydrogen ($FADH_2$) around the wound. The epithelialization metric can be used to define a boundary or perimeter associated with a wound. In embodiments, the epithelialization metric can define a spatial halo around a healing perimeter of the wound. The defined halo can comprise one or more light wavelength bands. In embodiments, the spatial halo can include a blue light wavelength ring.

The wound care metric can be used to gauge the status of a wound, to plan for wound care, and so on. In embodiments, the metric of wound monitoring can enable development of a wound care strategy. The wound care strategy can include types of wound coverings and frequency of wound monitoring and covering replacement; wound draining; courses of antibiotics and other medications; and so on. In other embodiments, the metric of wound monitoring can distinguish among wound repair, wound regeneration, and wound degeneration. The state of the wound can be used to determine an effectiveness of a wound care strategy, can indicate a need to alter or replace a care strategy, and the like. In embodiments, the distinguishing can be enabled by comparing ratios of nicotinamide adenine dinucleotide ($NAD^+$) to nicotinamide adenine dinucleotide plus hydrogen (NADH). The distinguishing can be enabled by comparing other ratios. In embodiments, the distinguishing can be enabled by comparing ratios of flavin adenine dinucleotide (FAD) to flavin adenine dinucleotide plus hydrogen ($FADH_2$).

More than one output signature can be generated for a wound sample. Further embodiments can include generating an additional output signature indicative of a condition of the wound sample. More than one additional output signature can be generated. The one or more additional output signatures can be based on one or more additional wound samples. In embodiments, the additional output signature can be generated at a later point in time than the output signature. The later point in time can be based on a number of hours, days, weeks, and so on. The output signature and the one or more additional output signatures can be analyzed and compared. In embodiments, the output signature and the additional output signature can be used to create a wound healing trajectory metric. The wound healing trajectory metric can track wound healing over a period of time to measure wound healing progress. In embodiments, the wound healing trajectory metric can be used to provide a recommended treatment option. The recommended treatment option can be adjusted based on the one or more additional output signatures. In embodiments, the recommended treatment option can include a debridement recommendation. Wound debridement can include biological, enzymatic, and autolytic debridement; mechanical debridement; sharp debridement; etc.

The analysis can include identifying granulation within the wound sample. The identifying granulation can include identifying an amount of granulation tissue, where the granulation tissue can fill in a wound. The granulation can be identified based on a measure of hemoglobin and collagen. The analysis can include identifying infection within the wound sample. Identifying infection is critical to effective wound treatment. The infection can be identified based on a measure of porphyrin, pyoverdine, slough, eschar, or an inflammation signature. The inflammation signature can be based on temperature, liquid content, and so on. The inflammation signature can include wound temperature and wound water content. The various analyses can contribute to an N-factor biophysical status of a wound sample. The identifying wound topology, inflammation, epithelialization, granulation, and infection can comprise a five-factor biophysical wound sample status.

The system 1000 can include a computer program product embodied in a non-transitory computer readable medium for wound care diagnosis, the computer program product comprising code which causes one or more processors to perform operations of: scanning a plurality of optical excitation ultraviolet light wavelength bands on a wound sample, wherein the wound sample exhibits optical spectral characteristics along the light wavelength spectrum; capturing excitation response wavelengths emitted by the wound sample in response to the plurality of optical excitation ultraviolet light wavelength bands, wherein the capturing is accomplished using an image sensor; measuring output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generating an output signature indicative of a condition of the wound sample, wherein the condition of the wound sample provides a metric of wound monitoring.

Each of the above methods may be executed on one or more processors on one or more computer systems. Embodiments may include various forms of distributed computing, client/server computing, and cloud-based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general-purpose hardware and computer instructions, and so on.

A programmable apparatus which executes any of the above-mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are limited to neither conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM); an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States, then the method is considered to be performed in the United States by virtue of the causal entity.

While the invention has been disclosed in connection with preferred embodiments shown and described in detail, various modifications and improvements thereon will become apparent to those skilled in the art. Accordingly, the foregoing examples should not limit the spirit and scope of the present invention; rather it should be understood in the broadest sense allowable by law.

What is claimed is:

1. A method for wound care diagnosis comprising:

scanning a plurality of optical excitation ultraviolet light wavelength bands on a wound sample, wherein the wound sample exhibits optical spectral characteristics along the light wavelength spectrum;

capturing excitation response wavelengths emitted by the wound sample in response to the plurality of optical excitation ultraviolet light wavelength bands, wherein the capturing is accomplished using an image sensor;

measuring output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generating an output signature indicative of a condition of the wound sample, wherein the condition of the wound sample provides a metric of wound monitoring.

2. The method of claim 1 wherein the excitation response wavelengths comprise a fluorescence signature for the wound sample.

3. The method of claim 1 wherein the metric of wound healing comprises an epithelialization metric.

4. The method of claim 3 wherein the epithelialization metric is based on detecting nicotinamide adenine dinucleotide plus hydrogen (NADH) around the wound.

5. The method of claim 4 wherein the epithelialization metric is further based on detecting a ratio of nicotinamide adenine dinucleotide ($NAD^+$) to nicotinamide adenine dinucleotide plus hydrogen (NADH) around the wound.

6. The method of claim 4 wherein the epithelialization metric is further based on detecting flavin adenine dinucleotide ($FADH_2$) around the wound.

7. The method of claim 6 wherein the epithelialization metric is further based on detecting a ratio of flavin adenine dinucleotide (FAD) to flavin adenine dinucleotide plus hydrogen ($FADH_2$) around the wound.

8. The method of claim 6 wherein the epithelialization metric defines a spatial halo around a healing perimeter of the wound.

9. The method of claim 8 wherein the spatial halo comprises a blue light wavelength ring.

10. The method of claim 6 wherein the $NAD^+$ and/or NADH optical excitation ultraviolet light wavelength bands comprise wavelengths substantially in the range of 325 nm to 400 nm.

11. The method of claim 10 wherein the FAD and/or $FADH_2$ optical excitation ultraviolet light wavelength bands comprise additional wavelengths substantially in the range of 400 nm to 475 nm.

12. The method of claim 1 wherein the excitation response wavelengths comprise wavelengths substantially in a range of 440 nm to 500 nm and 500 nm to 550 nm.

13. The method of claim 1 further comprising spatially registering the image to determine wound features contained in the wound sample.

14. The method of claim 13 wherein the wound features include a wound center and a wound edge.

15. The method of claim 1 wherein the metric of wound monitoring enables development of a wound care strategy.

16. The method of claim 1 wherein the metric of wound monitoring distinguishes among wound repair, wound regeneration, and wound degeneration.

17. The method of claim 16 wherein the distinguishing is enabled by comparing ratios of nicotinamide adenine dinucleotide ($NAD^+$) to nicotinamide adenine dinucleotide plus hydrogen (NADH).

18. The method of claim 16 wherein the distinguishing is enabled by comparing ratios of flavin adenine dinucleotide (FAD) to flavin adenine dinucleotide plus hydrogen ($FADH_2$).

19. The method of claim 1 further comprising generating an additional output signature indicative of a condition of the wound sample.

20. The method of claim 19 wherein the additional output signature is generated at a later point in time than the output signature.

21. The method of claim 20 wherein the output signature and the additional output signature are used to create a wound healing trajectory metric.

22. The method of claim 21 wherein the wound healing trajectory metric is used to provide a recommended treatment option.

23. The method of claim 22 wherein the recommended treatment option includes a debridement recommendation.

24. A computer program product embodied in a non-transitory computer readable medium for wound care diagnosis, the computer program product comprising code which causes one or more processors to perform operations of:

scanning a plurality of optical excitation ultraviolet light wavelength bands on a wound sample, wherein the wound sample exhibits optical spectral characteristics along the light wavelength spectrum;

capturing excitation response wavelengths emitted by the wound sample in response to the plurality of optical excitation ultraviolet light wavelength bands, wherein the capturing is accomplished using an image sensor;

measuring output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generating an output signature indicative of a condition of the wound sample, wherein the condition of the wound sample provides a metric of wound monitoring.

25. A computer system for wound care diagnosis comprising:

a memory which stores instructions;

one or more processors coupled to the memory wherein the one or more processors, when executing the instructions which are stored, are configured to:

scan a plurality of optical excitation ultraviolet light wavelength bands on a wound sample, wherein the wound sample exhibits optical spectral characteristics along the light wavelength spectrum;

capture excitation response wavelengths emitted by the wound sample in response to the plurality of optical excitation ultraviolet light wavelength bands, wherein the capturing is accomplished using an image sensor;

measure output values of a plurality of pixels of an image from the image sensor, wherein the image represents the excitation response wavelengths captured by the image sensor, wherein the measuring detects optical spectral characteristics of the wound sample, and wherein the optical spectral characteristics are in response to the plurality of optical excitation light wavelength bands; and generate an output signature indicative of a condition of the wound sample, wherein the condition of the wound sample provides a metric of wound monitoring.

* * * * *